US011337695B2

(12) United States Patent
Ye et al.

(10) Patent No.: US 11,337,695 B2
(45) Date of Patent: May 24, 2022

(54) STAPLE CARTRIDGE ASSEMBLY AND MEDICAL STAPLER USING THE STAPLE CARTRIDGE ASSEMBLY

(71) Applicant: Touchstone International Medical Science Co., LTD., Suzhou (CN)

(72) Inventors: Yanping Ye, Suzhou (CN); Tuo Shu, Suzhou (CN)

(73) Assignee: TOUCHSTONE INTERNATIONAL MEDICAL SCIENCE CO., LTD., Suzhou (CN)

( * ) Notice: Subject to any disclaimer, the term of this patent is extended or adjusted under 35 U.S.C. 154(b) by 0 days.

(21) Appl. No.: 16/772,799

(22) PCT Filed: Nov. 16, 2018

(86) PCT No.: PCT/CN2018/115821
§ 371 (c)(1),
(2) Date: Jun. 14, 2020

(87) PCT Pub. No.: WO2019/114495
PCT Pub. Date: Jun. 20, 2019

(65) Prior Publication Data
US 2021/0161527 A1  Jun. 3, 2021

(30) Foreign Application Priority Data

Dec. 14, 2017 (CN) .......................... 201711341435.2
Dec. 14, 2017 (CN) .......................... 201721746089.1
Dec. 14, 2017 (CN) .......................... 201721746900.6

(51) Int. Cl.
*A61B 17/072* (2006.01)
(52) U.S. Cl.
CPC .............. *A61B 17/07207* (2013.01); *A61B 2017/07257* (2013.01); *A61B 2017/07271* (2013.01); *A61B 2017/07285* (2013.01)

(58) Field of Classification Search
CPC ............ A61B 17/072; A61B 17/07207; A61B 2017/07257; A61B 2017/07271;
(Continued)

(56) References Cited
U.S. PATENT DOCUMENTS 5,465,896 A    11/1995  Allen et al.
8,701,960 B1 *  4/2014  Manoux ........... A61B 17/07207
                                                227/175.1
(Continued)

FOREIGN PATENT DOCUMENTS

CN    101797174 A    8/2010
CN    201668441 U    12/2010
(Continued)

*Primary Examiner* — Stephen F. Gerrity
*Assistant Examiner* — Linda J Hodge
(74) *Attorney, Agent, or Firm* — Cheng-Ju Chiang

(57) ABSTRACT

The present invention discloses a staple cartridge assembly and a medical stapler using the staple cartridge assembly. A first jaw is provided with a limiting portion; a cutter is provided with a securing portion; when a firing block is located at a proximal end of a staple cartridge assembly, a cutting push rod drives the cutter and the firing block together to move; when the firing block is located at the distal end of the staple cartridge assembly, a driving mechanism drives the cutter and the first jaw to move relative to each other; and the limiting portion and the securing portion resist against each other to restrict the cutter from continuing moving toward the distal end of the staple cartridge assembly. As a result, doctors can be effectively prevented from closing the stapler when the replacement of the fired staple cartridge assembly is not completed.

19 Claims, 30 Drawing Sheets

(58) Field of Classification Search
CPC .......... A61B 2017/07285; A61B 2017/00473; A61B 2017/07278; A61B 2090/0814
USPC .......... 227/175.2–175.4, 177.1, 180.1, 181.1
See application file for complete search history.

(56) References Cited

U.S. PATENT DOCUMENTS

| | | | |
|---|---|---|---|
| 2007/0102475 A1* | 5/2007 | Ortiz | A61B 17/07207 227/175.2 |
| 2011/0257679 A1 | 10/2011 | Ishitsuki et al. | |
| 2015/0173755 A1* | 6/2015 | Baxter, III | A61B 17/07207 227/180.1 |
| 2015/0316431 A1* | 11/2015 | Collins | A61B 90/98 606/219 |
| 2016/0183948 A1* | 6/2016 | Shelton, IV | A61B 17/072 227/175.2 |

FOREIGN PATENT DOCUMENTS

| | | |
|---|---|---|
| CN | 202409017 U | 9/2012 |
| CN | 102743201 A | 10/2012 |
| CN | 203220400 U | 10/2013 |
| CN | 103860220 A | 6/2014 |
| CN | 103860222 A | 6/2014 |
| CN | 204207795 U | 3/2015 |
| CN | 204364049 U | 6/2015 |
| CN | 107334504 A | 11/2017 |
| CN | 208851552 U | 5/2019 |

\* cited by examiner

STAPLE CARTRIDGE ASSEMBLY AND MEDICAL STAPLER USING THE STAPLE CARTRIDGE ASSEMBLY

CROSS-REFERENCE TO RELATED APPLICATION

This application is a 35 U.S.C. § 371 National Phase conversion of International (PCT) Patent Application No. PCT/CN2018/115821, filed on Nov. 16, 2018, which claims priority to Chinese patent application No. 201711341435.2 filed on Dec. 14, 2017 and entitled "STAPLE CARTRIDGE ASSEMBLY AND MEDICAL STAPLER USING THE STAPLE CARTRIDGE ASSEMBLY", Chinese patent application No. 201721746900.6 filed on Dec. 14, 2017 and entitled "STAPLE CARTRIDGE ASSEMBLY AND MEDICAL STAPLER USING THE STAPLE CARTRIDGE ASSEMBLY", and Chinese patent application No. 201721746089.1 filed on Dec. 14, 2017 and entitled "STAPLE CARTRIDGE ASSEMBLY AND MEDICAL STAPLER USING THE STAPLE CARTRIDGE ASSEMBLY", the entire contents of which are incorporated herein by reference. The PCT International Patent Application was filed and published in Chinese.

TECHNICAL FIELD

The present invention belongs to the field of medical instruments, and more particularly, relates to a staple cartridge assembly and a medical stapler using the staple cartridge assembly.

BACKGROUND

A medical stapler is a medical instrument that is commonly used in surgical operations on intestinal and other physiological tissues. It is an alternative medical device to the traditional manual suture device. Owing to the development of modern technology and the improvement of production technology, the medical stapler currently used in clinical practice is reliable in quality and convenient to use with appropriate tightness, and especially has the advantages such as high suture speed, easy operation and few side effects and surgical complications. Sometimes, the medical stapler can be used to remove the lesions of tumors that could not be surgically removed in the past. Therefore, the medical stapler is highly favored and admired by clinical surgeons at home and abroad. Its performance variation has a crucial effect on the overall surgical results.

In the prior art, a linear medical stapler for the minimally invasive surgery includes an instrument platform and a staple cartridge assembly cooperating with the instrument platform. The instrument platform includes a housing and a firing handle pivotally disposed on the housing. A relatively movable pushing rod is provided in the housing and can push the staple cartridge assembly located at a front end of the housing for cutting and suturing.

Specifically, the staple cartridge assembly includes a staple cartridge channel and an anvil pivotally connected to the staple cartridge channel. A staple cartridge is disposed detachably on the staple cartridge channel.

The staple cartridge assembly further includes a staple cartridge connector for connecting the instrument platform, the staple cartridge channel, the anvil, and the staple cartridge. A relatively movable cutting push rod is disposed in the staple cartridge connector. The cutting push rod is mated with the pushing rod and a cutter is fixed to a distal end of the cutting push rod. The cutter advances to close the staple cartridge and the anvil for cutting tissues between the staple cartridge and the anvil, and to drive a firing block for pushing staple pushing pieces out of the staple cartridge in sequence; and the staple pushing pieces in turn push staples out of the staple cartridge to allow the staples to be stapled on the tissues.

After the cutting and suturing operations above are completed by a doctor, the medical stapler needs to be reset at first, and then the staple cartridge assembly needs to be replaced for the next cutting and suturing procedures using the medical stapler. However, some careless or inexperienced doctors may perform the operations followed without replacing the fired staple cartridge assembly, which may lead to medical accidents, that is, suturing is not performed after the cutting.

SUMMARY

An object of the present invention is to provide a staple cartridge assembly and a medical stapler using the staple cartridge assembly.

To achieve one of the above objects of the present invention, an embodiment of the present invention provides a staple cartridge assembly, comprising:

a staple cartridge connector, which comprises a housing and a cutting push rod located in the housing;

a first jaw and a second jaw, both of which are located at a distal end of the staple cartridge connector and are capable of being opened/closed;

a firing block, which is movably disposed in the first jaw or the second jaw;

a cutter, which is located at a distal end of the cutting push rod, and can push the firing block to move under the action of the cutting push rod; and a driving mechanism, wherein the first jaw is provided with a limiting portion at a proximal end; the cutter is provided with a securing portion; when the firing block is located at a proximal end of the staple cartridge assembly, the cutting push rod drives the cutter and the firing block together to move toward a distal end of the staple cartridge assembly; when the firing block is located at the distal end of the staple cartridge assembly, the driving mechanism drives the cutter and the first jaw to move relative to each other; and the limiting portion and the securing portion resist against each other to restrict the cutter from continuing moving toward the distal end of the staple cartridge assembly.

As a further improvement to an embodiment of the present invention, when the firing block is located at the proximal end of the staple cartridge assembly and the cutter does not contact the firing block, the driving mechanism drives the cutter and the first jaw to move relative to each other, and the securing portion enters the limiting portion; and then when the cutting push rod drives the cutter to continue moving toward the distal end of the staple cartridge assembly, the firing block abuts against and drives the cutter to shift toward a side away from the first jaw, and the securing portion is separated from the limiting portion.

As a further improvement to an embodiment of the present invention, the first jaw comprises a staple cartridge channel and a staple cartridge, which are connected; the second jaw is an anvil; and the limiting portion is located at the staple cartridge channel.

As a further improvement to an embodiment of the present invention, the driving mechanism is a driving member connected to the housing; the cutting push rod is provided with a boss at a side close to the driving member; and when the boss moves toward the distal end of the staple cartridge assembly and to the driving member, the driving member drives the cutting push rod to shift toward a side away from the driving member, so that the cutter shifts toward a side close to the staple cartridge channel to allow the securing portion to enter the limiting portion.

As a further improvement to an embodiment of the present invention, the firing block is provided with a first resisting portion at a proximal end; the cutter is provided with a second resisting portion at a distal end; and when the first resisting portion and the second resisting portion resist against each other, the firing block drives the cutter to move toward a side away from the staple cartridge channel to allow the securing portion to be separated from the limiting portion.

As a further improvement to an embodiment of the present invention, at least one of the first resisting portion and the second resisting portion is provided with a guiding portion.

As a further improvement to an embodiment of the present invention, one of the securing portion and the limiting portion is a protrusion, and the other is a groove.

As a further improvement to an embodiment of the present invention, the securing portion is a protrusion, which comprises a first slope at a proximal end; the limiting portion is a groove, which comprises a second slope at a proximal end; and the first slope and the second slope are the same in gradient.

As a further improvement to an embodiment of the present invention, the protrusion comprises a first plane at a distal end; the groove comprises a second plane at a distal end; and when the protrusion is located at the most distal end of the groove, the first plane and the second plane interfere with each other to restrict the protrusion from being separated from the groove.

As a further improvement to an embodiment of the present invention, the driving member is an elastic piece; when the boss moves toward the distal end of the staple cartridge assembly and to the elastic piece, the elastic piece drives the cutting push rod to shift toward a side away from the elastic piece; and when the firing block abuts against the cutter, the firing block drives the cutter to shift toward a side away from the staple cartridge channel to allow the cutting push rod to reset, and the boss drives the elastic piece to deform toward a side away from the boss.

As a further improvement to an embodiment of the present invention, the cutting push rod is provided with notches on two sides of the boss; and when the elastic piece is separated from the boss, the elastic piece enters the notches and the elastic piece maintains an initial state.

As a further improvement to an embodiment of the present invention, the elastic piece is a U-shaped elastic piece.

As a further improvement to an embodiment of the present invention, the driving mechanism is a compression spring that is located at the proximal end of the staple cartridge assembly and connected to the staple cartridge channel and the anvil; when the cutting push rod drives the cutter to move toward the distal end of the staple cartridge assembly and to the limiting portion, the compression spring drives the staple cartridge channel to shift toward a side close to the securing portion to allow the securing portion to enter the limiting portion.

As a further improvement to an embodiment of the present invention, the firing block is provided with a first contact portion at its proximal end; the cutter is provided with a second contact portion at its distal end; and when the first contact portion and the second contact portion resist against each other, the firing block drives the cutter to shift toward a side away from the staple cartridge channel to allow the securing portion to be separated from the limiting portion.

As a further improvement to an embodiment of the present invention, at least one of the first contact portion and the second contact portion is provided with a guiding portion.

As a further improvement to an embodiment of the present invention, the limiting portion comprises a receiving groove located in an outer surface of the staple cartridge channel; the securing portion comprises a first end of the cutter; the first end is located at the outer surface of the staple cartridge channel; when the cutter moves to the receiving groove, the compression spring acts on the staple cartridge channel to allow the first end to enter the receiving groove; and when the firing block abuts against the cutter, the firing block drives the first end to shift toward a side away from the staple cartridge channel to allow the first end to be separated from the receiving groove.

As a further improvement to an embodiment of the present invention, the limiting portion further comprises a recessed portion located at a distal end of the receiving groove; the securing portion further comprises a bulging portion located at a distal end of the first end; and when the first end is located in the receiving groove and the cutter continues to move toward the distal end of the staple cartridge assembly, the bulging portion and the recessed portion are engaged with each other.

As a further improvement to an embodiment of the present invention, the limiting portion comprises two recessed portions that are symmetrically distributed at the distal end of the receiving groove; and the securing portion comprises two bulging portions that are symmetrically distributed at the distal end of the first end.

As a further improvement to an embodiment of the present invention, the driving mechanism comprises two compression springs that are symmetrically distributed on two sides of the cutter.

To achieve one of the above objects of the present invention, an embodiment of the present invention provides a medical stapler, which comprises the staple cartridge assembly according to any of the technical solutions above.

Compared with the prior art, the present invention has the following beneficial effects: at least in a secondary firing process in an embodiment of the present invention, the driving mechanism drives the cutter and the first jaw to move relative to each other, so that the limiting portion and the securing portion resist against each other to restrict the cutter from continuing moving toward the distal end of the staple cartridge assembly. As a result, doctors can be effectively prevented from closing the medical stapler without replacing the fired staple cartridge assembly, thereby avoiding medical accidents or damages to normal tissues; and a simple and effective structure is achieved.

DETAILED DESCRIPTION

Figure 1:
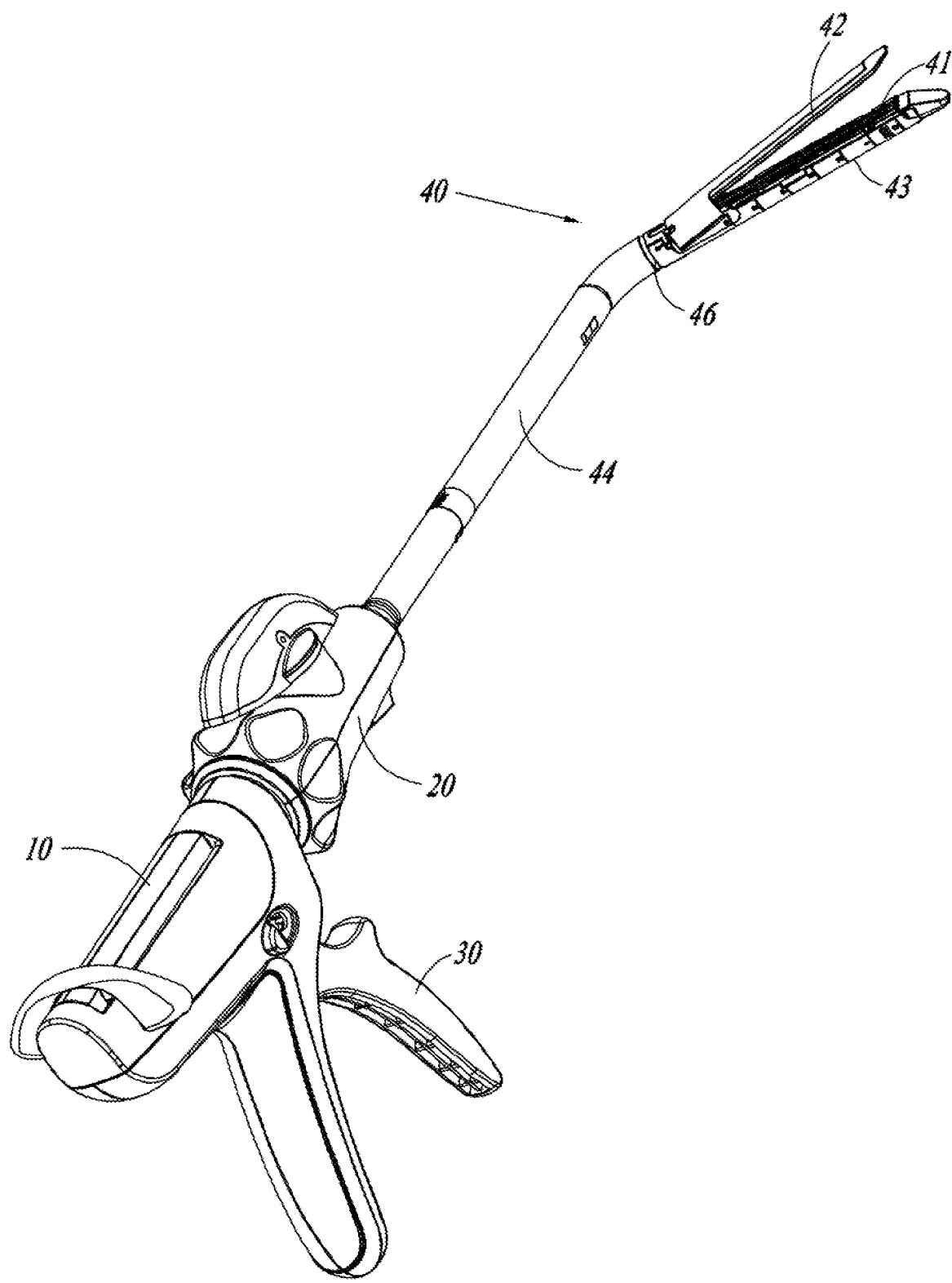
FIG. 1 is a schematically structural diagram of a medical stapler according to an embodiment of the present invention.

The present invention will be described in detail below with reference to the specific embodiments shown in the drawings. However, these embodiments are not intended to limit the present invention. Any structural, method, or functional variations made by those of ordinary skills in the art according to these embodiments shall fall within the protection scope of the present invention.

In the present invention, terms indicating positions and directions are described with an instrument operator as a reference, where an end close to the operator is designated as a proximal end, and an end away from the operator is designated as a distal end.

In each illustration of the present invention, for ease of illustration, certain dimensions of a structure or portion may be scaled up relative to other structures or portions. Therefore, this is merely intended to illustrate the basic structure of the subject matter of the present invention.

As used herein, "upper", "above", "lower", "below" and other terms indicating relative positions in space are used to describe a relationship between a unit or feature relative to another unit or feature as shown in the drawings for ease of illustration. The terms indicating the relative positions in space may be intended to include various orientations of a device in use or operation, in addition to the orientations shown in the drawings. For example, if the device in a drawing is turned over, a unit described as "below" or "beneath" other units or features will be "above" other units or features. Accordingly, the exemplary term "below" may encompass both the orientations of above and below. The device may be oriented in other ways (rotated by 90 degrees or facing other orientations), and the space-related description terms used herein will be correspondingly explained.

In the embodiments of the present invention, the medical stapler according to the present invention is explained in detail by taking an endoscopic surgical cutting stapler as an example. However, it should be noted that the technical spirit involved in the following embodiments can be alternatively applied to other forms of staplers.

Figure 2:
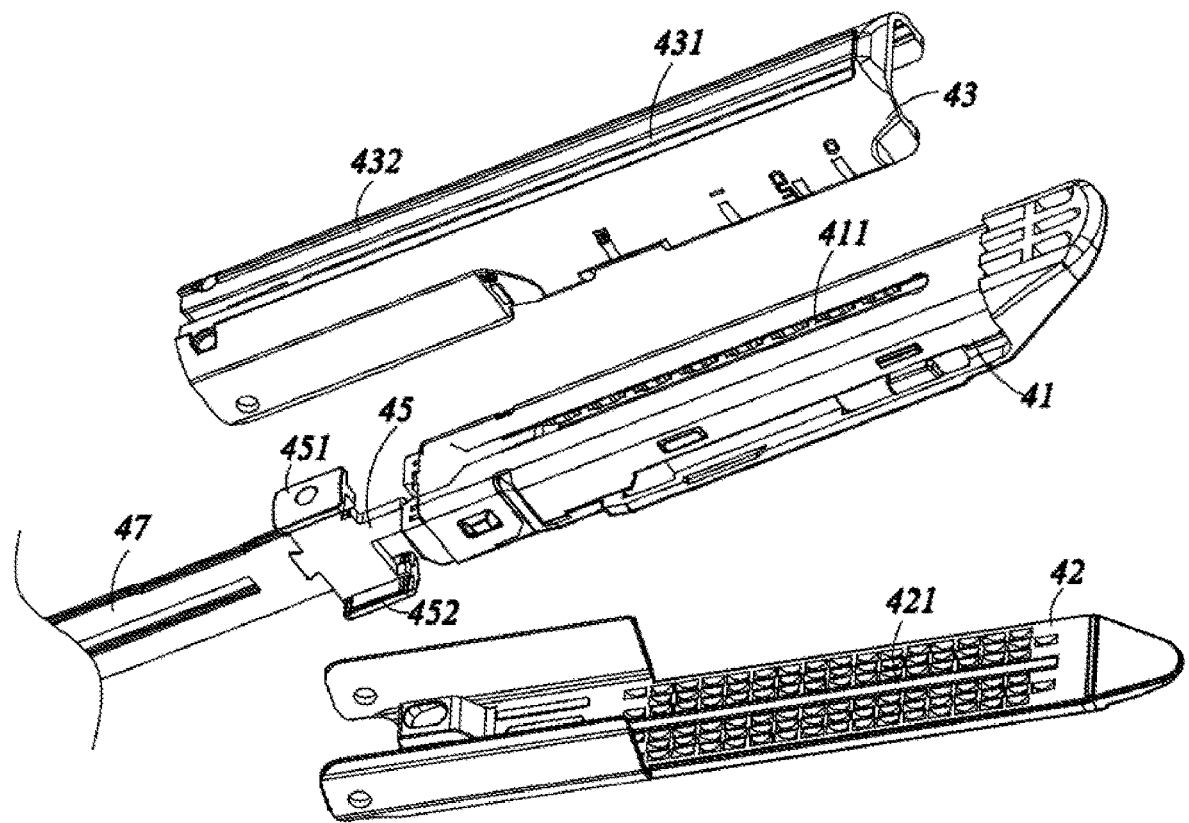
FIG. 2 is a schematically partially exploded structural diagram of a staple cartridge assembly according to an embodiment of the present invention.
Figure 3:
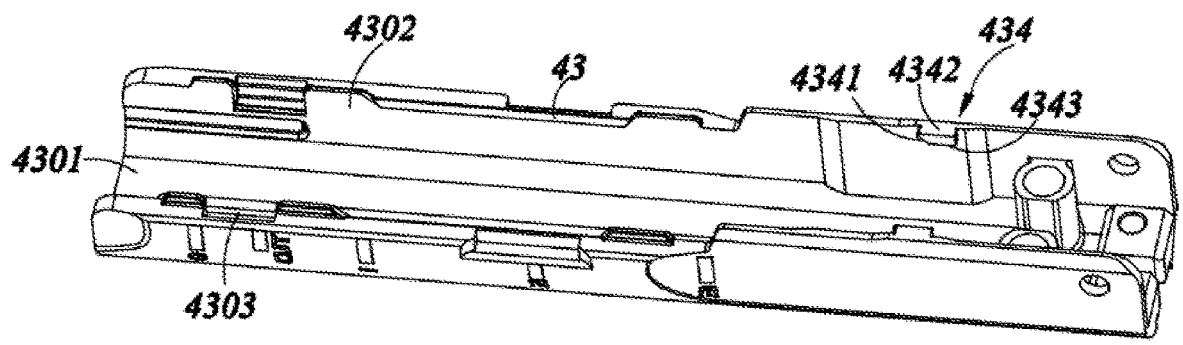
FIG. 3 is a schematic diagram of a staple cartridge channel according to an embodiment of the present invention.
Figure 4:
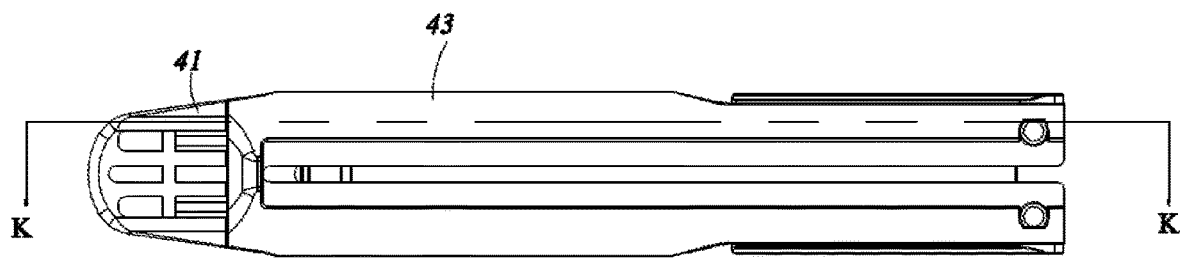
FIG. 4 is a schematic diagram of a combination of a staple cartridge channel, a staple cartridge and an anvil according to an embodiment of the present invention.
Figure 5:
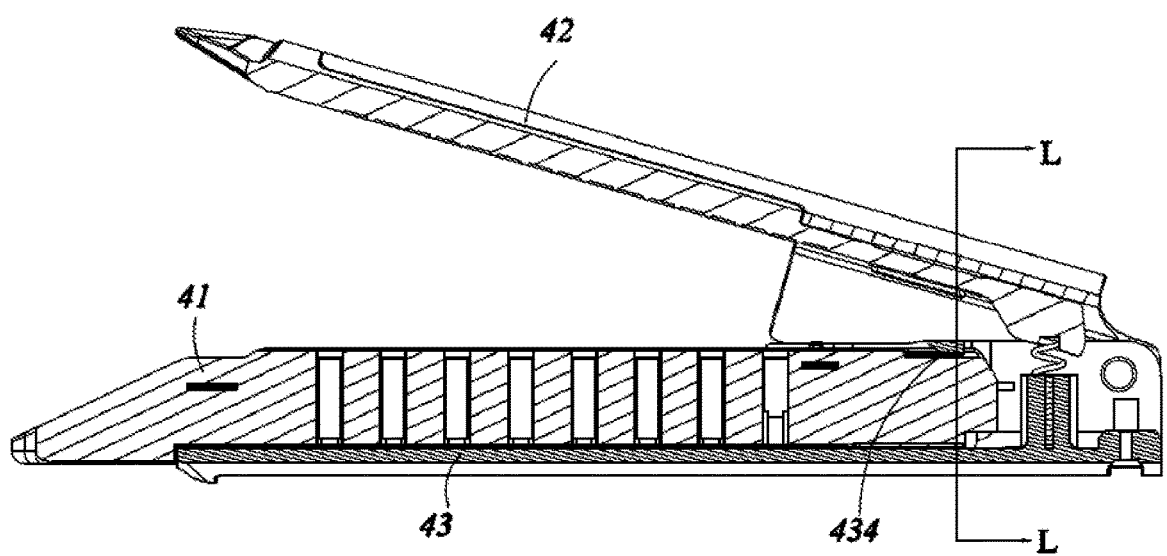
FIG. 5 is a sectional view along K-K in FIG. 4.
Figure 6:
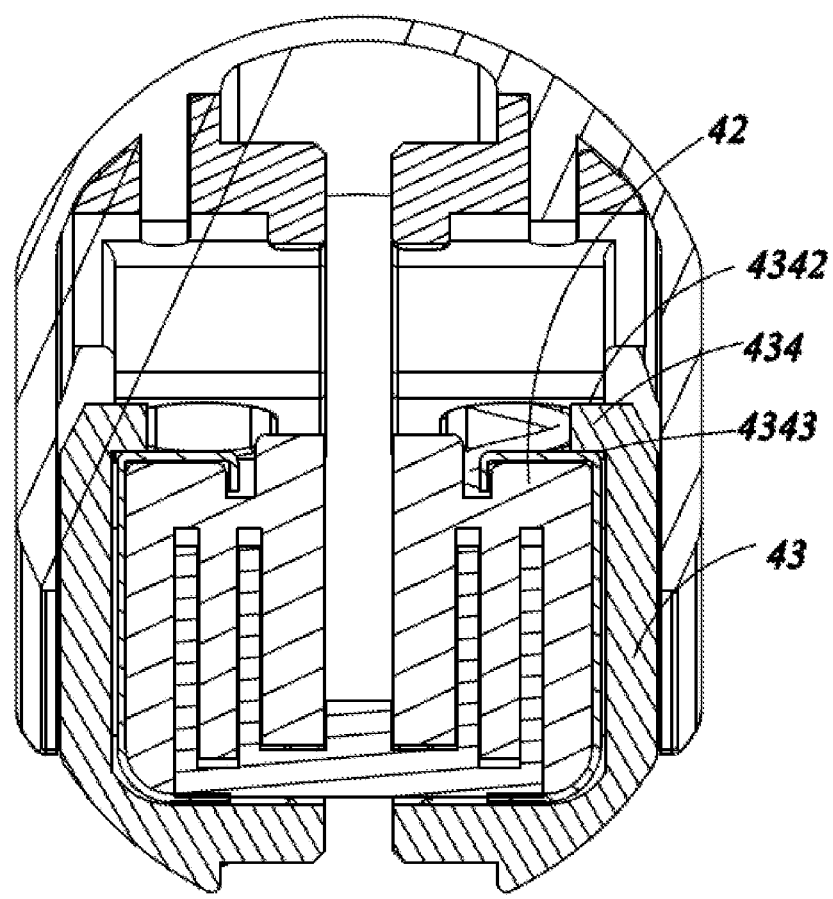
FIG. 6 is a sectional view along L-L in FIG. 5.

As shown in FIG. 1 and FIG. 2, the medical stapler is configured to apply a plurality of staples to the physiological tissues of a human body while correspondingly cutting the physiological tissues. The medical stapler includes an instrument platform 10, a rotation ring 20 mated with the instrument platform 10, and a firing handle 30 pivotally connected to the instrument platform 10.

A pushing rod is disposed in the instrument platform 10, and the pushing rod may move relative to a housing of the instrument platform 10 under the action of the firing handle 30.

The instrument platform 10 is further provided with a staple cartridge assembly 40 at a distal end, and the staple cartridge assembly 40 is detachably connected to the instrument platform 10.

The staple cartridge assembly 40 includes a staple cartridge 41, an anvil 42, a staple cartridge channel 43, a staple cartridge connector 44, a cutter 45, and a joint 46 disposed at a distal end of the staple cartridge connector 44. By controlling the rotation direction and rotation angle of the joint 46, an area defined by the staple cartridge 41 and the anvil 42 may rotate relative to the staple cartridge connector 44 to adapt to a multi-angle cutting and stapling operation.

Of course, there can also be no joint 46 in the instrument where the staple cartridge assembly 40 cannot swing.

The staple cartridge channel 43 defines a support channel to receive the staple cartridge 41 therein in a mountable manner, and the staple cartridge channel 43 is configured to connect the staple cartridge 41 to the staple cartridge connector 44.

In this embodiment, the staple cartridge 41 and the anvil 42 are configured to be rotatable relatively. When the staple cartridge 41 and the anvil 42 are rotated to an open state, target physiological tissues to be operated can be placed between the staple cartridge 41 and the anvil 42; and then, by rotating the staple cartridge 41 and the anvil 42 to a closed state, the target physiological tissues therebetween are clamped for subsequent cutting and suturing operations.

When the medical stapler/staple cartridge assembly 40 is in an initial state, the tail at a proximal end of the anvil 42 was applied an external force to keep the anvil 42 and the staple cartridge 41 open, and the cutter 45 is located at the proximal end of the staple cartridge assembly 40.

When the medical stapler/staple cartridge assembly 40 is in a closed state, the anvil 42 and the staple cartridge 41 are closed under the driving of the cutter 45, and may clamp the target physiological tissues therebetween; and the cutter 45 moves a certain distance toward the distal end of the medical stapler/staple cartridge assembly 40 with respect to the cutter 45 in the initial state, but remains at the proximal end of the staple cartridge assembly 40 on a whole.

When the medical stapler/staple cartridge assembly 40 is in a firing state, the anvil 42 and the staple cartridge 41 still keep closed; and the cutter 45 moves from the proximal end of the staple cartridge assembly 40 to the distal end to cut the clamped physiological tissues, and may be limited to stop moving at the distal end of the staple cartridge assembly 40.

As shown in FIG. 2, the staple cartridge channel 43 includes a first resisting surface 432, which is away from the anvil 42 and cooperates with a first end 451 of the cutter 45; and the anvil 42 includes a second resisting face, which opposites to an anvil face and cooperates with a second end 452 of the cutter 45.

The staple cartridge 41, the anvil 42, and the staple cartridge channel 43 are formed with cutter receiving grooves 411, 421 and 431 respectively that cooperate with the cutter 45. The cutter receiving grooves 411, 421 and 431 extend from the proximal ends of the staple cartridge 41, the anvil 42, and the staple cartridge channel 43 to the distal ends, respectively. When the staple cartridge 41 and the anvil 42 are closed, the cutter receiving grooves 411, 421 and 431 may cooperate to form a channel, which allows the cutter 45 to move in a direction from the proximal end of the staple cartridge assembly 40 toward the distal end thereof, or in a direction from the distal end of the staple cartridge assembly 40 toward the proximal end thereof.

The staple cartridge assembly 40 further includes a cutting push rod 47 connected to the proximal end of the cutter 45. The cutting push rod 47 may drive the cutter 45 to move from the proximal ends to the distal ends, or from the distal ends to the proximal ends, of the cutter receiving grooves 411, 421 and 431. In this process, the cutter receiving grooves 411, 421 and 431 provide a movement path for the cutter 45 and the cutting push rod 47 while guiding the cutter 45 and the cutting push rod 47. As the area defined by the anvil 42 and the staple cartridge 41 rotates by a certain angle relative to the staple cartridge connector 44, the cutting push rod 47 is also bent at a certain angle, so that the cutter 45 may smoothly move toward the distal end of the medical stapler.

In this embodiment, referring to FIG. 3 to FIG. 6, the staple cartridge channel 43 is provided with a stop portion 434 at a proximal end. When the staple cartridge channel 43 and the staple cartridge 41 cooperate with each other, the stop portion 434 restricts the staple cartridge 41 from being separated from the staple cartridge channel 43 along a direction in which the staple cartridge 41 and the staple cartridge channel 43 are superposed.

Here, the proximal end of the staple cartridge 41 is suppressed by the stop portion 434, and during the firing of the medical stapler, the proximal end of the staple cartridge 41 will not deform and upwarp, so that the entire firing operation process is smoother.

The staple cartridge channel 43 is surrounded by a bottom 4301 and two side walls (4302, 4303) connected to the bottom 4301, and the stop portion 434 are located at sides of the side walls (4302, 4303) away from the bottom 4301 respectively.

The staple cartridge assembly 40 includes two stop portions 434 at the two side walls (4302, 4303) respectively, and the two stop portions 434 are disposed symmetrically to stably limit the proximal end of the staple cartridge 41.

In this embodiment, the stop portion 434 is a projection 434, which has one end connected to one side wall 4302, and the other end extending toward the other side wall 4303.

The projection 434 is provided with a chamfered portion 4341 at a distal end.

Here, the chamfered portion 4341 is a slope 4341 inclined toward the proximal end of the bottom 4301 of the staple cartridge channel 43.

When the staple cartridge 41 is assembled into the staple cartridge channel 43, the proximal end of the staple cartridge 41 is first inserted into the staple cartridge channel 43. At this time, the proximal end of the staple cartridge 41 may be assembled into the staple cartridge channel 43 through the slope 4341.

A first surface 4343 of the projection 434 close to the bottom 4301 is a plane, and is parallel to the bottom 4301. As such, when the staple cartridge 41 is assembled into the staple cartridge channel 43, the projection 434 may be stably fitted to the surface of the staple cartridge 41.

A second surface 4342 of the projection 434 away from the bottom 4301 is a plane, and is flush with the side edges of the side walls (4302, 4303) away from the bottom 4301. As such, the projection 434 is prevented from blocking the anvil 42 during the closing of the staple cartridge assembly 40.

Figure 7:
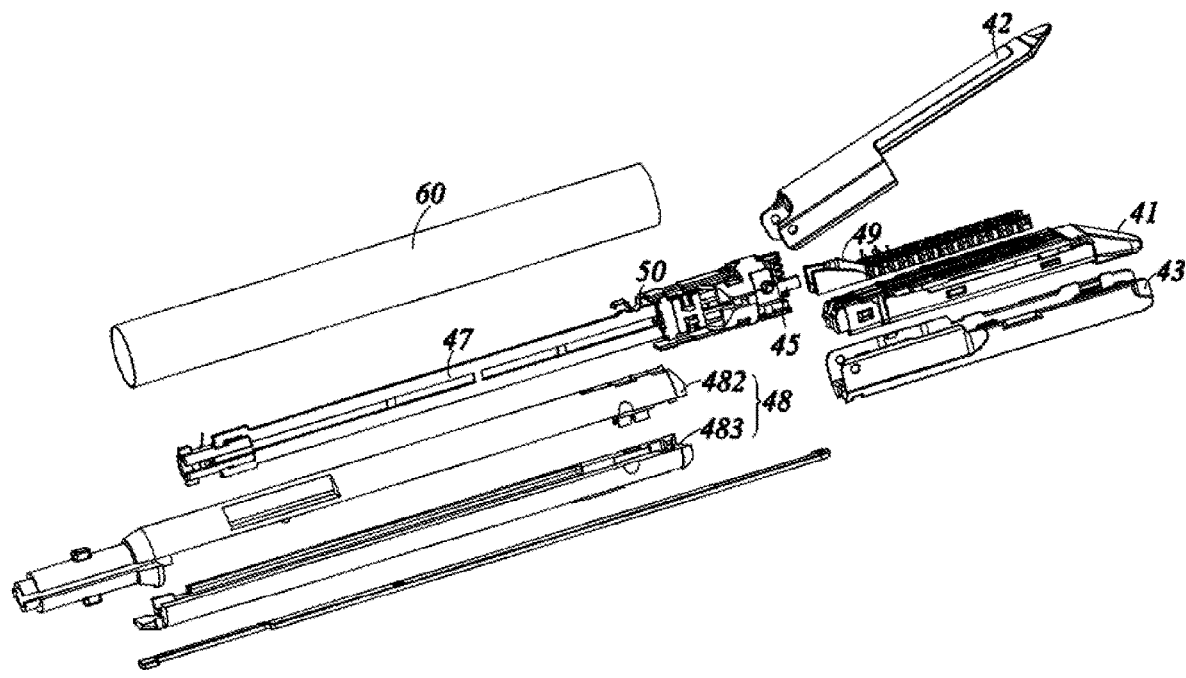
FIG. 7 is a schematically exploded diagram of a staple cartridge assembly according to a first embodiment of the present invention.
Figure 8:
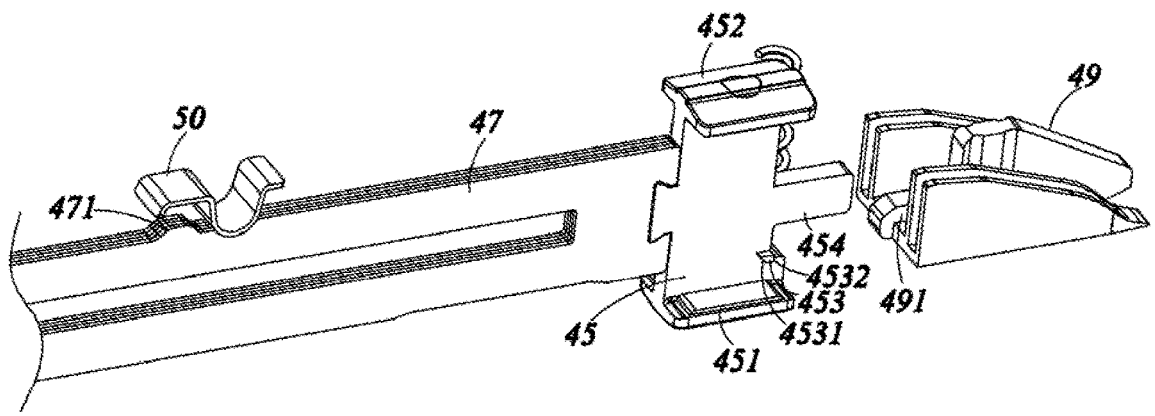
FIG. 8 is a schematic diagram of a combination of a cutting push rod, a cutter and a firing block according to the first embodiment of the present invention.
Figure 9:
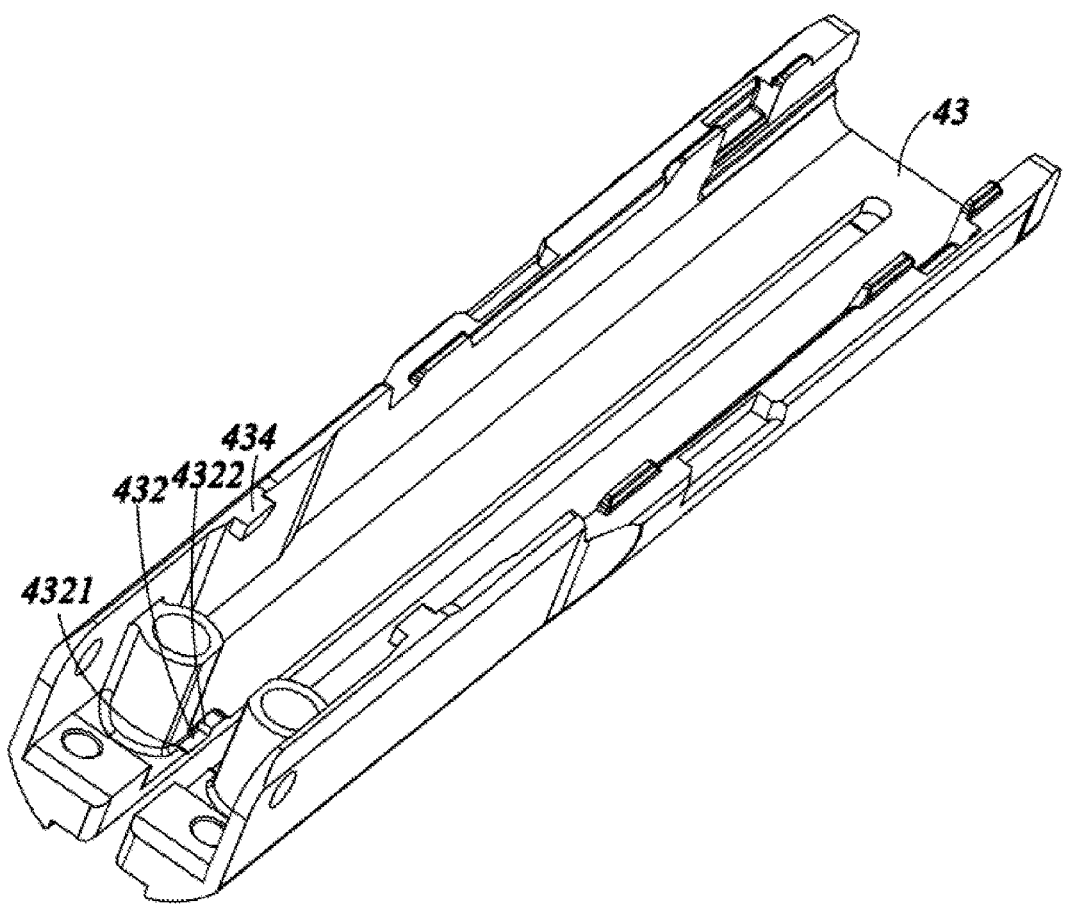
FIG. 9 is a schematic diagram of a staple cartridge channel according to the first embodiment of the present invention.
Figure 10:
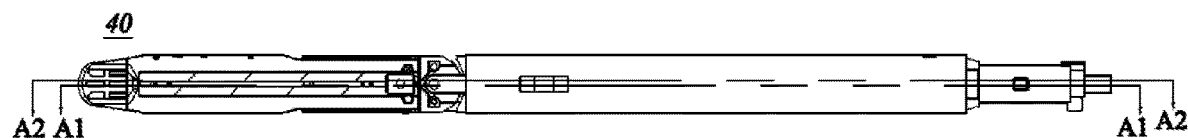
FIG. 10 is a schematic diagram of the staple cartridge assembly according to the first embodiment of the present invention, which is in an initial state.
Figure 11:
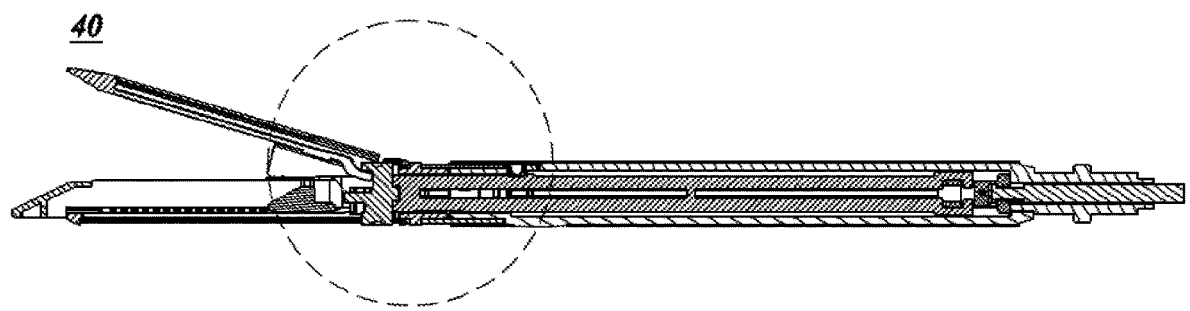
FIG. 11 is a sectional view along A1-A1 in FIG. 10.

Referring to FIG. 7 to FIG. 9, in an embodiment of the present invention, the staple cartridge assembly 40 further includes a first jaw, a second jaw, a firing block 49 and a driving mechanism 50, wherein the first and second jaws are located at the distal end of the staple cartridge connector 44 and are capable of being opened/closed.

The firing block 49 is movably disposed in the first jaw or the second jaw. The cutter 45 can push the firing block 49 to move under the action of the cutting push rod 47, thereby sequentially push staple pushing pieces out of the staple cartridge 41, and the staple pushing pieces in turn push staples out of the staple cartridge 41 and staple the staples to the tissues.

Here, with an example that the first jaw includes the staple cartridge channel 43 and the staple cartridge 41 which are connected and the second jaw is the anvil 42, the firing block 49 is located in the staple cartridge 42, but it is not limited thereto.

Referring to FIG. 8 and FIG. 9, the first jaw is provided with a limiting portion 432 at its proximal end, and the cutter 45 is provided with a securing portion 453.

Here, the description is given with an example that the staple cartridge channel 43 is provided with a limiting portion 432 at the proximal end, but it is not limited thereto.

When the firing block 49 is located at a proximal end of the staple cartridge assembly 40, the cutting push rod 47 drives the cutter 45 and the firing block 49 together to move toward a distal end of the staple cartridge assembly 40. When the firing block 49 is located at the distal end of the staple cartridge assembly 40, the driving mechanism 50 drives the cutter 45 and the first jaw to move relative to each other. The limiting portion 432 and the securing portion 453 resist against each other to restrict the cutter 45 from continuing moving toward the distal end of the staple cartridge assembly 40.

Here, when the cutter 45 moves toward the distal end of the staple cartridge assembly 40 for the first time (that is, the firing block 49 is located at the proximal end of the staple cartridge assembly), the cutting push rod 47 drives the cutter 45 and the firing block 49 together to move toward the distal end of the staple cartridge assembly 40. When the cutter 45 moves toward the distal end of the staple cartridge assembly 40 for the second time (that is, replacement with a new staple cartridge assembly 40 is not completed, and the firing block 49 has completed firing and is located at the distal end of the staple cartridge assembly 40), the driving mechanism 50 may drive the securing portion 453 and the limiting portion 432 to resist against each other to restrict the cutter 45 from continuing moving toward the distal end of the staple cartridge assembly 40. Therefore, the doctor is effectively prevented from firing again after the firing has been completed, thereby avoiding medical accidents or damages to normal tissues; and a simple and effective structure is achieved.

Next, the cooperation between the cutter 45 and the firing block 49 when the cutter 45 moves toward the distal end of the staple cartridge assembly 40 for the first time will be described.

In an example, a distance between the firing block 49 and the cutter 45 is large in an initial state. When the firing block 49 is located at the proximal end of the staple cartridge assembly 40 and the cutter 45 does not contact the firing block 49, the driving mechanism 50 drives the cutter 45 and the first jaw to move relative to each other; and the securing portion 453 enters the limiting portion 432 to cause the staple cartridge assembly 40 to enter a secure state. Then, when the cutting push rod 47 drives the cutter 45 to continue moving toward the distal end of the staple cartridge assembly 40, the firing block 49 abuts against and drives the cutter 45 to shift toward a side away from the first jaw, and the securing portion 453 is separated from the limiting portion 432, thereby releasing the staple cartridge assembly 40 from the secure state.

That is to say, during the first movement of the cutter 45 toward the distal end of the staple cartridge assembly 40, the securing portion 453 has entered the limiting portion 432, and then, the firing block 49 acts on the cutter 45 to drive the securing portion 453 to get separated from the limiting portion 432 for subsequent normal cutting and suturing operation, but it is not limited thereto.

In another example, the distance between the firing block 49 and the cutter 45 is small in the initial state. When the cutter 45 moves toward the distal end of the staple cartridge assembly 40 for the first time, the firing block 49 has contacted the cutter 45 and driven the cutter 45 to move to the distal end of the staple cartridge assembly 40, before the securing portion 453 enters the limiting portion 432 to cause the staple cartridge assembly enter the secure state. That is, during the first movement of the cutter 45 toward the distal end of the staple cartridge assembly 40, the limiting portion 432 can not restrict the securing portion 453, and the instrument may be fired at this time. After the firing is completed, the firing block 49 remains at the distal end of the staple cartridge assembly 40. If the cutter 45 is driven to move again toward the distal end of the staple cartridge assembly 40 at this time, the driving mechanism 50 may drive the limiting portion 432 and the securing portion 453 to resist against each other to cause the staple cartridge assembly 40 to enter the secure state, since the firing block 49 is located at the distal end of the staple cartridge assembly 40 and is unable to act on the cutter 45.

There are many embodiments of the staple cartridge assembly 40 of the present invention. Two of the embodiments of the staple cartridge assembly 40 of the present invention will be described below.

For convenience of explanation, both embodiments are described with an example that "a distance between the firing block 49 and the cutter 45 is relatively larger". That is, before the firing block 49 interacts with the cutter 45, the securing portion 453 enters the limiting portion 432 to cause the staple cartridge assembly 40 to enter the secure state.

In conjunction with FIG. 10 to FIG. 34 which show the schematic diagrams of the staple cartridge assembly 40 according to a first embodiment of the present invention.

In this embodiment, with reference to FIG. 10 to FIG. 19, the driving mechanism 50 is a driving member 50 connected to the housing 48, and the cutting push rod 47 is provided with a boss 471 at a side close to the driving member 50.

When the boss 471 moves toward the distal end of the staple cartridge assembly 40 and to the driving member 50, the driving member 50 drives the cutting push rod 47 to shift toward a side away from the driving member 50, so that the cutter 45 shifts toward a side close to the staple cartridge channel 43 to cause the securing portion 453 to enter the limiting portion 432.

Figure 12:
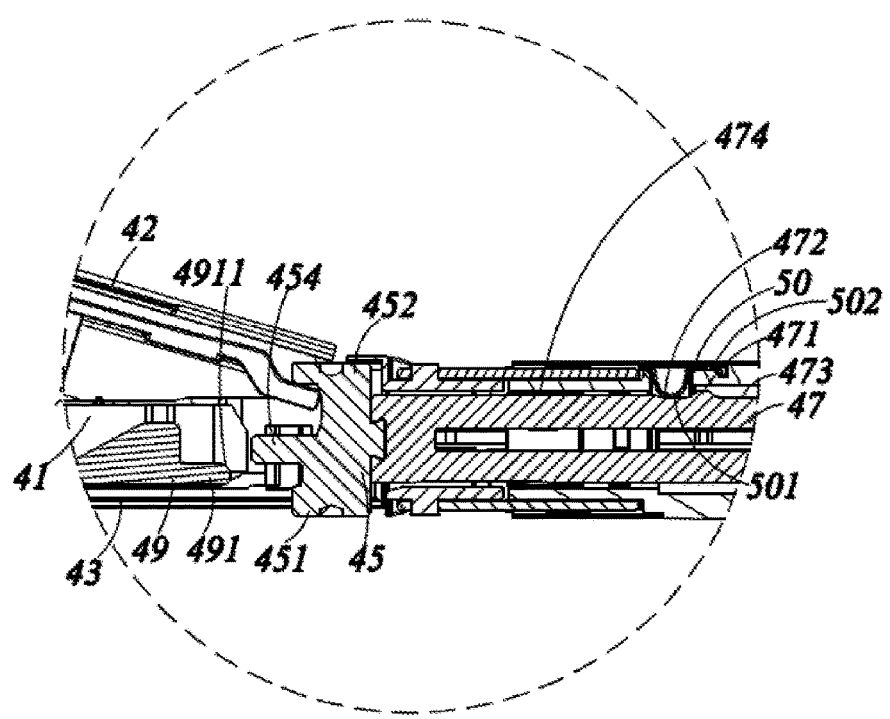
FIG. 12 is an enlarged view of a partial area in FIG. 11.
Figure 13:
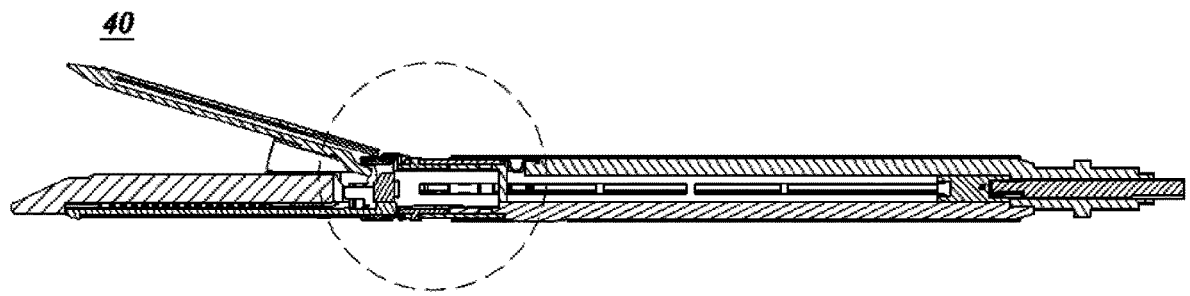
FIG. 13 is a sectional view along A2-A2 in FIG. 10.

Referring to FIG. 12, the firing block 49 is provided with a first resisting portion 491 at a proximal end, and the cutter 45 is provided with a second resisting portion 454 at a distal end. When the first resisting portion 491 and the second resisting portion 454 resist against each other, the firing block 49 drives the cutter 45 to shift toward a side away from the staple cartridge channel 43, so that the securing portion 453 is separated from the limiting portion 432.

Here, the second resisting portion 454 is a raised post extending in a direction from the proximal end of the staple cartridge assembly 40 toward the distal end.

At least one of the first resisting portion 491 and the second resisting portion 454 is provided with a guiding portion. Here, an arcuate face 4911 at the proximal end of the first resisting portion 491 is taken as the guiding portion 4911, and when the cutter 45 moves toward the distal end of the staple cartridge assembly 40 relative to the firing block 49, the firing block 49 smoothly lifts up the cutter 45 through the guiding portion 4911, thereby causing the securing portion 453 to move up and get separated from the limiting portion 432.

One of the securing portion 453 and the limiting portion 432 is a protrusion, and the other is a groove.

Figure 14:
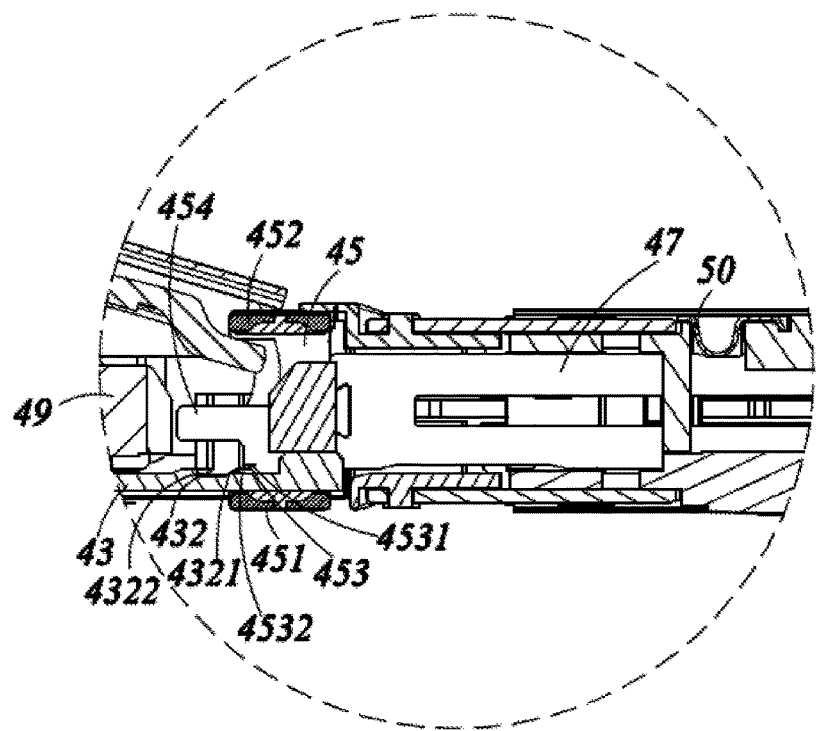
FIG. 14 is an enlarged view of a partial area in FIG. 13.
Figure 15:
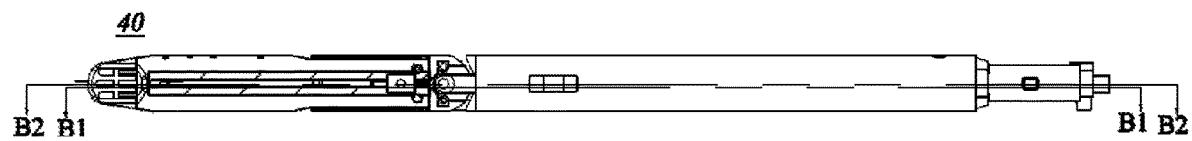
FIG. 15 is a schematic diagram of the staple cartridge assembly according to the first embodiment of the present invention, which enters a closing process.
Figure 16:
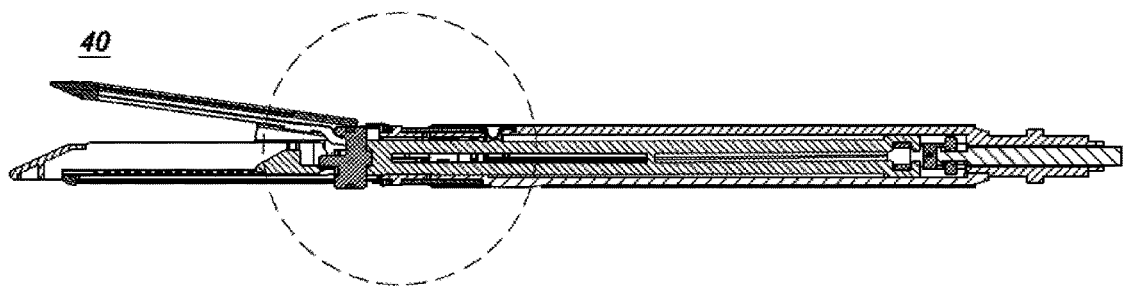
FIG. 16 is a sectional view along B1-B1 in FIG. 15.
Figure 17:
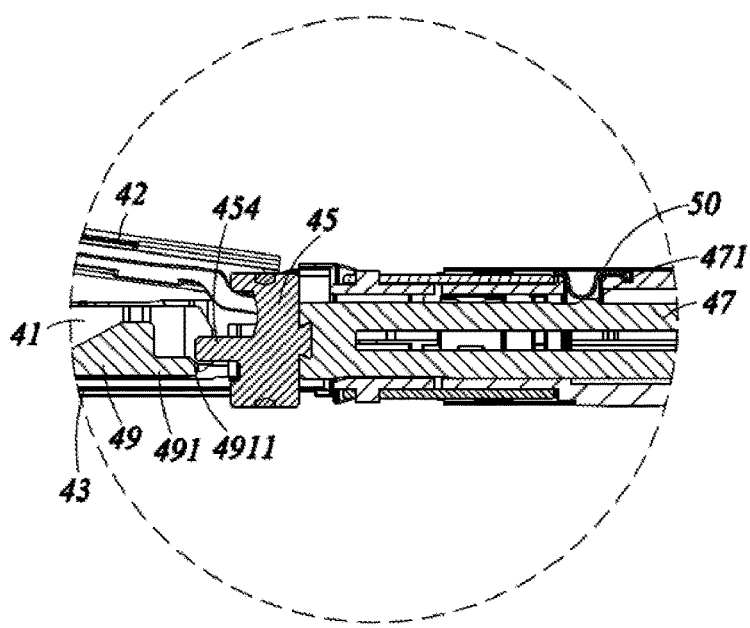
FIG. 17 is an enlarged view of a partial area in FIG. 16.
Figure 18:
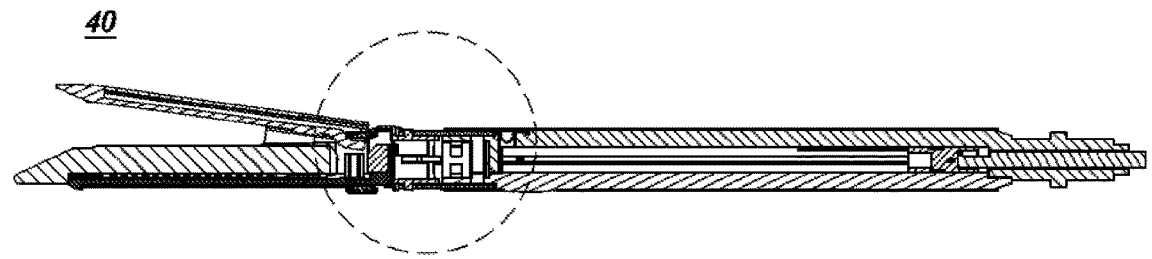
FIG. 18 is a sectional view along B2-B2 in FIG. 15.
Figure 19:
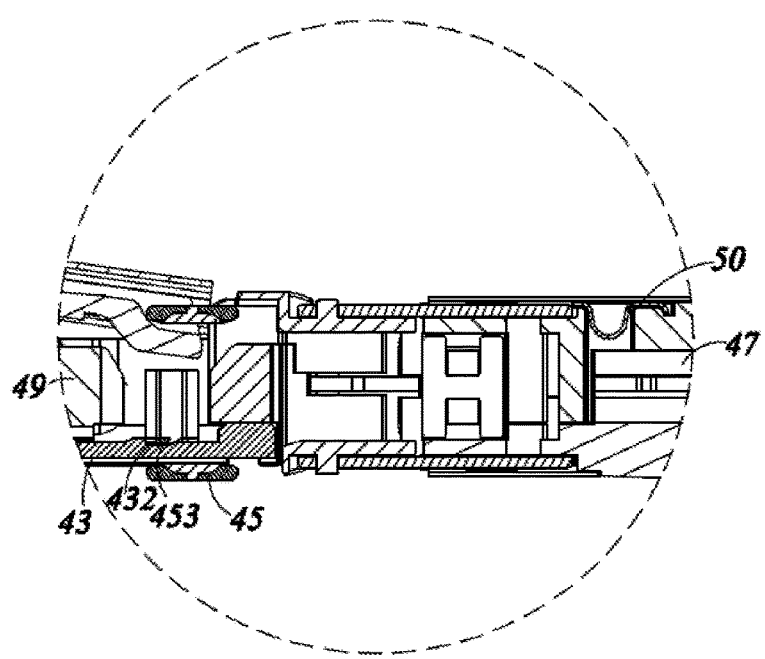
FIG. 19 is an enlarged view of a partial area in FIG. 18.
Figure 20:
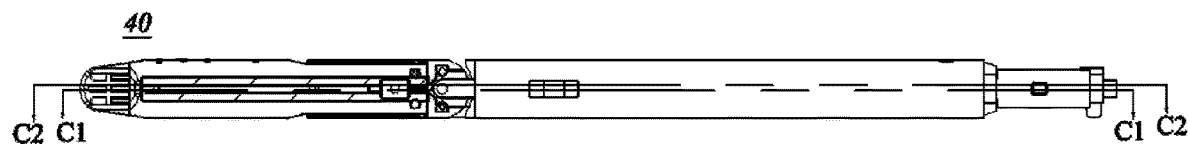
FIG. 20 is a schematic diagram of the staple cartridge assembly according to the first embodiment of the present invention, which is continuously closed.
Figure 21:
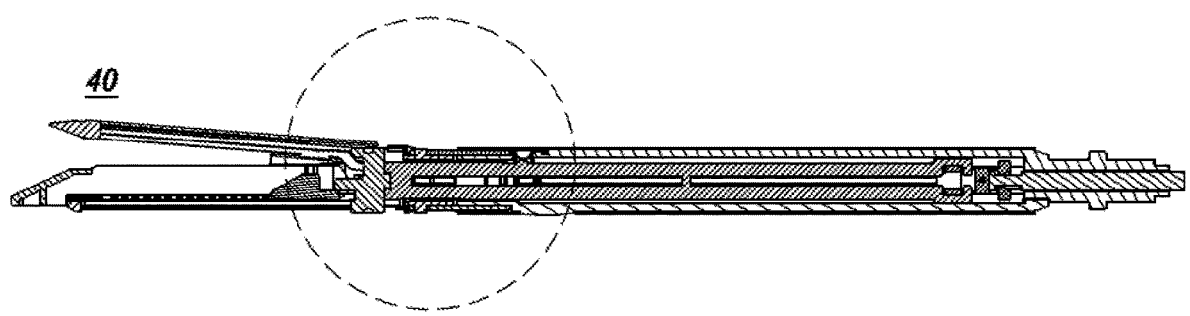
FIG. 21 is a sectional view along C1-C1 in FIG. 20.
Figure 22:
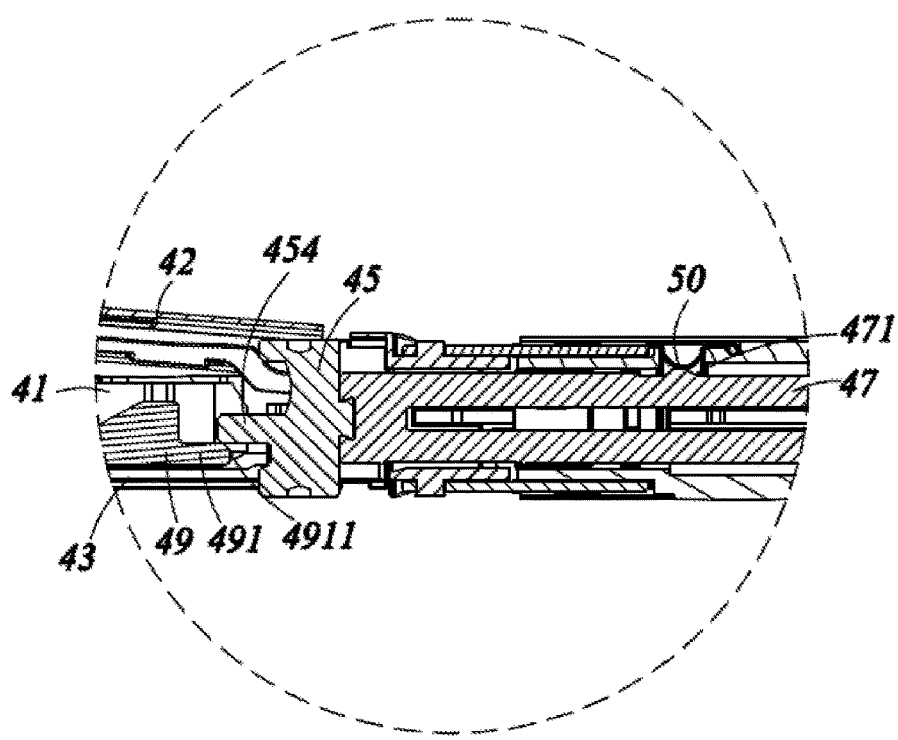
FIG. 22 is an enlarged view of a partial area in FIG. 21.
Figure 23:
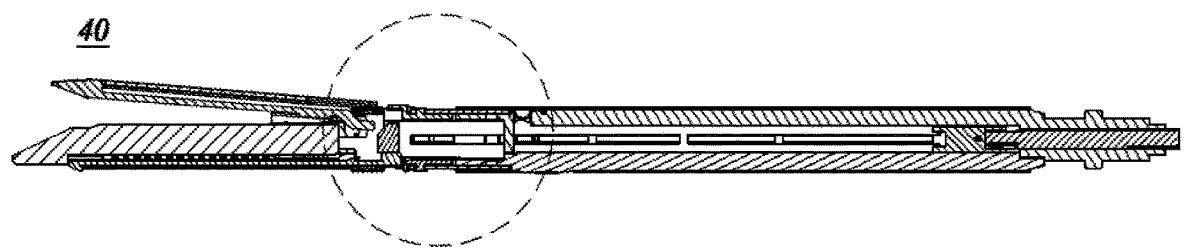
FIG. 23 is a sectional view along C2-C2 in FIG. 20.
Figure 24:
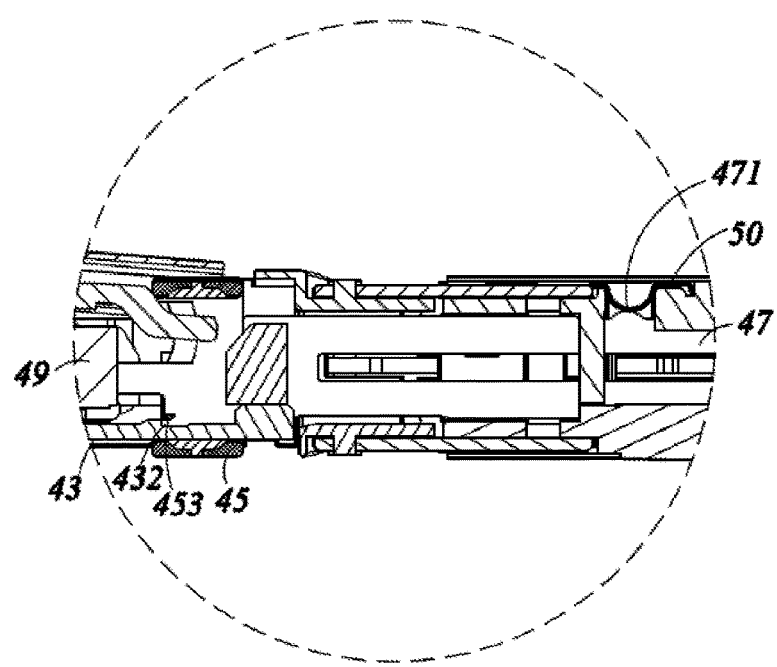
FIG. 24 is an enlarged view of a partial area in FIG. 23.
Figure 25:
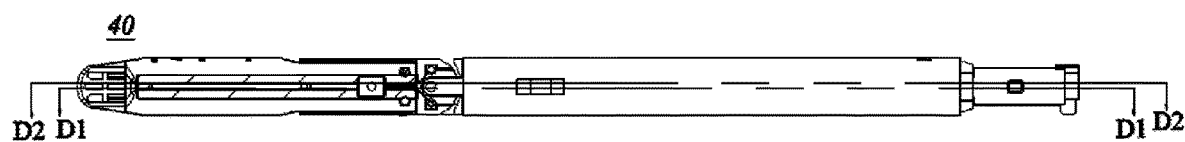
FIG. 25 is a schematic diagram of the staple cartridge assembly according to the first embodiment of the present invention, which is fully closed.
Figure 26:
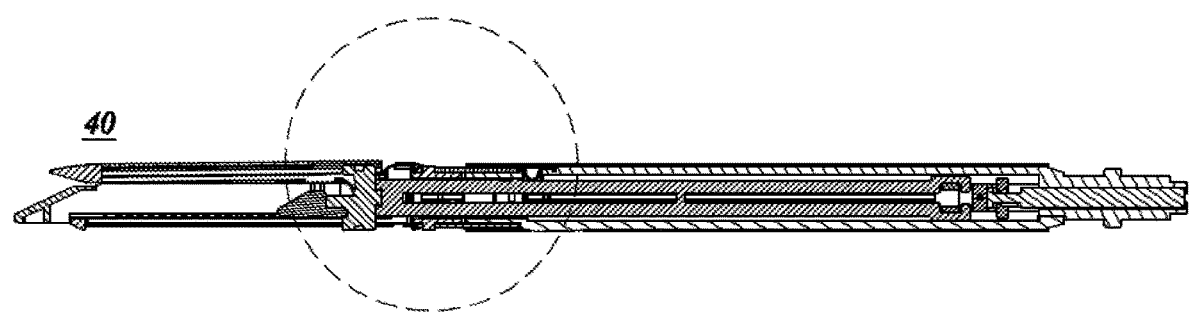
FIG. 26 is a sectional view along D1-D1 in FIG. 25.
Figure 27:
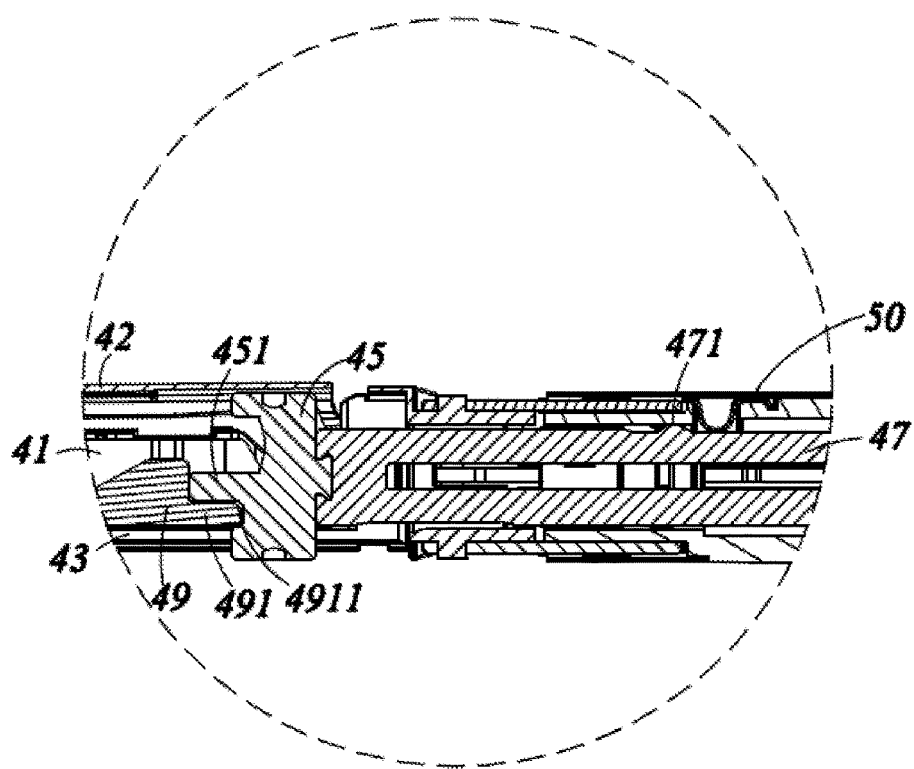
FIG. 27 is an enlarged view of a partial area in FIG. 26.
Figure 28:
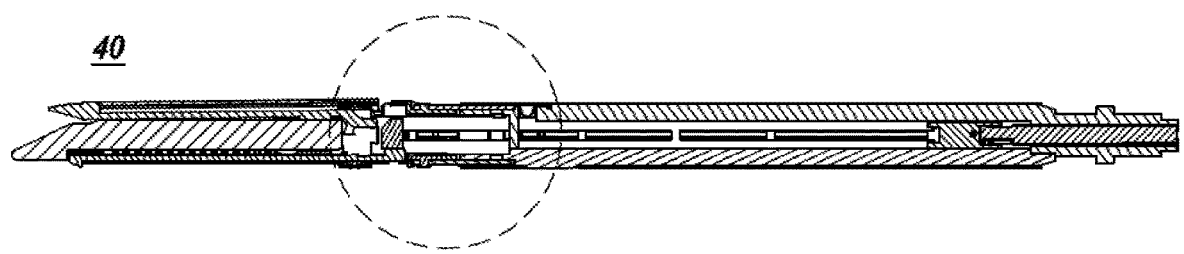
FIG. 28 is a sectional view along D2-D2 in FIG. 25.
Figure 29:
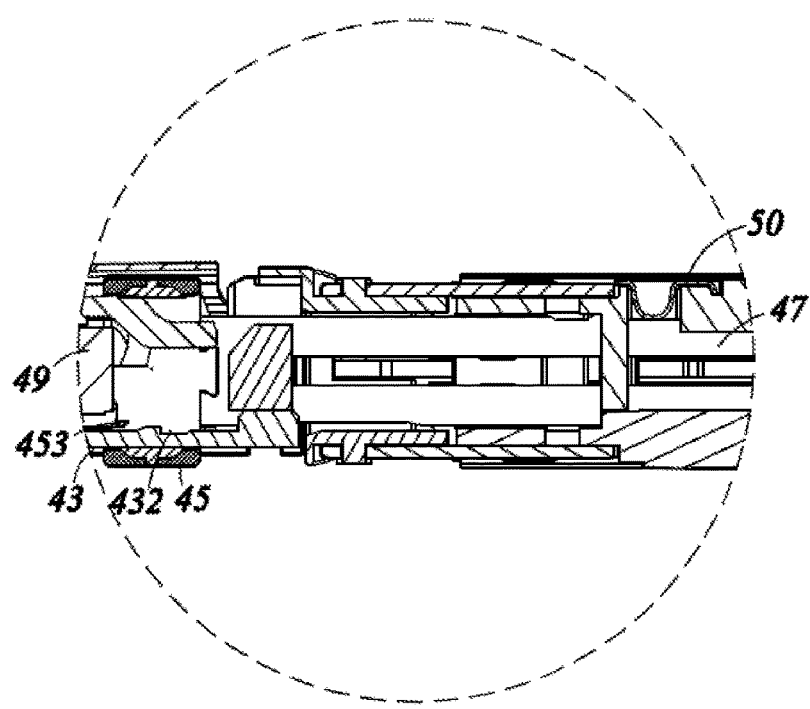
FIG. 29 is an enlarged view of a partial area in FIG. 28.
Figure 30:
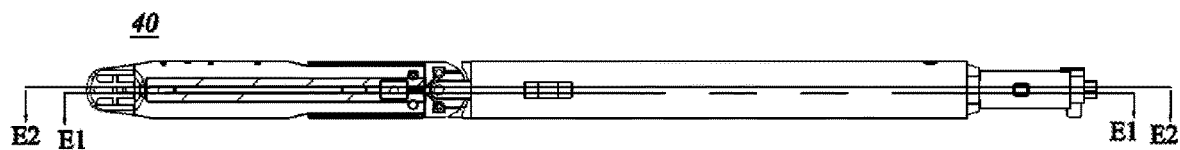
FIG. 30 is a schematic diagram of the staple cartridge assembly according to the first embodiment of the present invention, which enters a secondary closing process.
Figure 31:
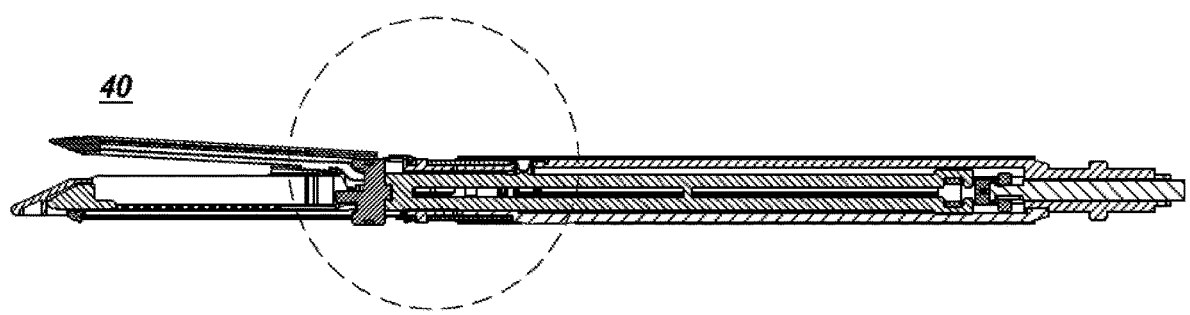
FIG. 31 is a sectional view along E1-E1 in FIG. 30.
Figure 32:
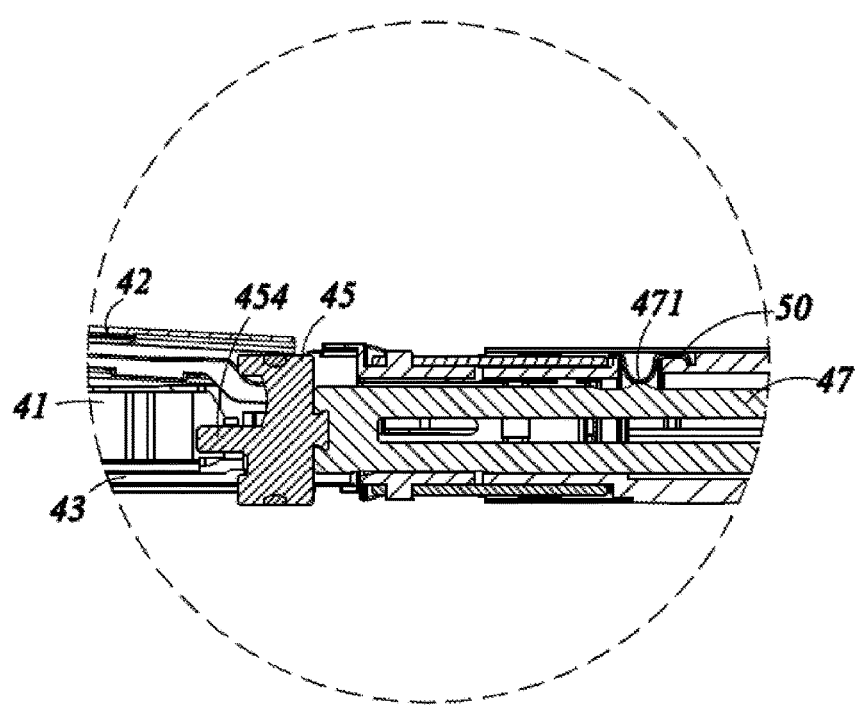
FIG. 32 is an enlarged view of a partial area in FIG. 31.
Figure 33:
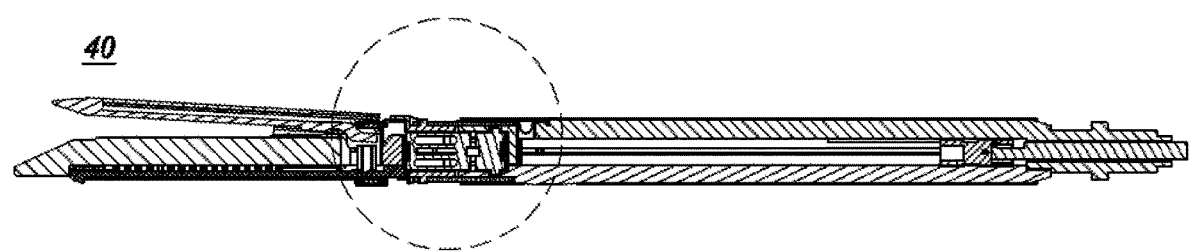
FIG. 33 is a sectional view along E2-E2 in FIG. 30.
Figure 34:
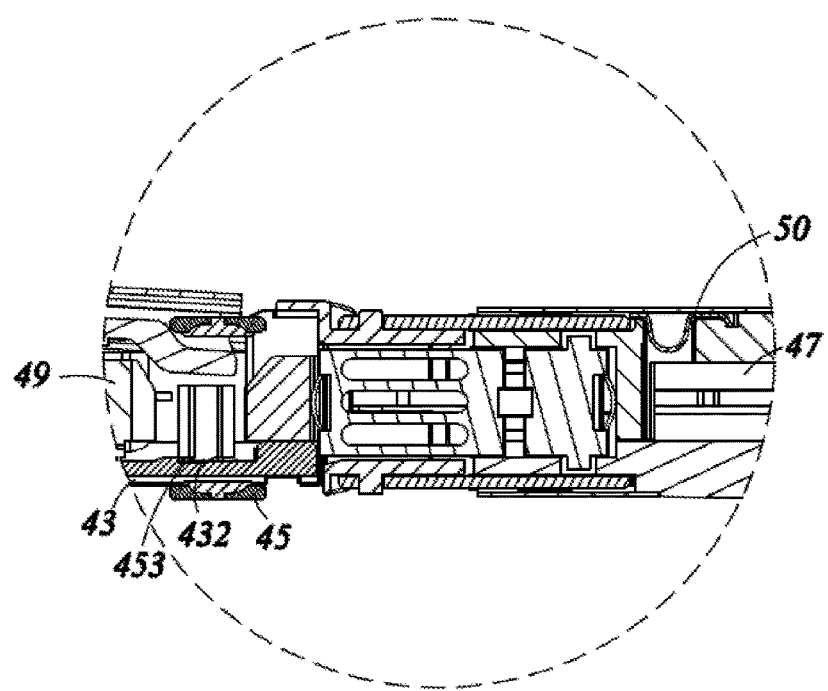
FIG. 34 is an enlarged view of a partial area in FIG. 33.

In this embodiment, referring to FIG. 14 (in conjunction with FIG. 8 and FIG. 9), the securing portion 453 is a protrusion 453. Preferably, two protrusions 453 are symmetrically disposed on the left and right sides of the cutter 45, with each protrusion 453 including a first slope 4531 at a proximal end.

The limiting portion 432 is a groove 432. Preferably, two grooves 432 are symmetrically disposed on two sides of the cutter receiving groove 431 of the staple cartridge channel 43, with each groove 432 including a second slope 4321 at a proximal end. The first slope 4531 and the second slope 4321 are the same in gradient.

The protrusion 453 includes a first plane 4532 at a distal end, and the groove 432 includes a second plane 4322 at a distal end.

Preferably, an included angle between the first plane 4532 and a bottom face of the protrusion 453 and having an opening facing a proximal direction is an acute angle or a right angle. Similarly, an included angle between the second plane 4522 and a bottom face of the groove 453 is an acute angle or a right angle. As such, a more reliable limiting effect is achieved between the limiting portion 432 and the securing portion 453.

Here, when the cutter 45 moves toward the distal end of the staple cartridge assembly 40 for the first time, the protrusion 453 enters the groove 432. As the cutter 45 continues moving toward the distal end, the firing block 49 in turn drives the cutter 45 to move up, and the protrusion 453 and the groove 432 do not interfere with each other in the closing direction of the staple cartridge assembly 40, so that the protrusion 453 may be separated from the groove 432 easily. When the cutter 45 retreats toward the proximal end of the staple cartridge assembly 40 and the protrusion 453 enters the groove 432 again, the protrusion 453 is separated from the groove 432 by means of the interaction between the first slope 4531 and the second slope 4321. When the cutter 45 moves toward the distal end of the staple cartridge assembly 40 again, the protrusion 453 enters the groove 432, the firing block 49 at this time is located at the distal end of the staple cartridge assembly 40, and the cutter 45 may not move up. As the protrusion 453 gradually moves to the most distal end of the groove 432, the first plane 4532 and the second plane 4322 interfere with each other, so that the protrusion 453 may not get separated from the groove 432.

In this embodiment, the driving member 50 is an elastic piece 50. In conjunction with FIGS. 15 to 19, when the boss 471 moves toward the distal end of the staple cartridge assembly 40 and to the elastic piece 50, the elastic piece 50 drives the cutting push rod 47 to shift toward a side away from the elastic piece 50 with the elastic piece 50 kept at the initial state, and the securing portion 453 enters the limiting portion 432. Referring to FIGS. 20 to 24, when the firing block 49 abuts against the cutter 45, the firing block 49 drives the cutter 45 to shift toward a side away from the staple cartridge channel 43 so as to reset the cutting push rod 47. The boss 471 drives the elastic piece 50 to deform toward a side away from the boss 471, and thus the securing portion 453 is separated from the limiting portion 432.

The cutting push rod 47 is provided with notches (a first notch 472 and a second notch 473, in combination with FIG. 12) on two sides of the boss 471. When the elastic piece 50 is separated from the boss 471, the elastic piece 50 enters the notches and is kept at the initial state.

It should be noted that the notches may extend from the boss 471 to two ends of the cutting push rod 47 respectively.

Here, in a direction from the distal end toward the proximal end of the staple cartridge assembly, the side portion of the cutting push rod 47 includes a smoothing portion 474, the first notch 472, the boss 471, and a second notch 473 in sequence. The first notch 472 is flush with the second notch 473. The smoothing portion 474 is higher than the first notch 472. A route that the elastic piece 50 passes through includes the first notch 472, the boss 471, and the second notch 473.

The advantages of this design are as follows: (1) the elastic piece 50 does not apply a force to the cutting push rod 47 at the first notch 472 and the second notch 473, thereby avoiding affecting a traveling path of the cutting push rod 47 at these areas; (2) the elastic piece 50 has a certain degree of deformation to adapt to a narrow space in the housing 48; and (3) the smoothing portion 474 is maintained at a large height to ensure the strength of the cutting push rod 47.

Preferably, the elastic piece 50 is a U-shaped elastic piece. Two movable ends 502 (in conjunction with FIG. 12) of the elastic piece 50 are respectively engaged with the housing 48. A resisting end 501 of the elastic piece 50 is disposed close to the cutting push rod 47 and interacts with the boss 471.

It can be understood that in other embodiments, the driving member 50 may be a rigid member. At this time, when the boss 471 moves toward the distal end of the staple cartridge assembly 40 and to the rigid member, the rigid member drives the cutting push rod 47 to shift toward a side away from the rigid member, and the securing portion 453 enters the limiting portion 432. When the firing block 49 abuts against the cutter 45, the firing block 49 drives the cutter 45 to shift toward a side away from the staple cartridge channel 43 for resetting the cutting push rod 47. Meanwhile, the rigid member is separated from the boss 471, and the securing portion 453 is separated from the limiting portion 432.

The working principle of the staple cartridge assembly 40 of this embodiment will be described in detail below.

Referring to FIGS. 10 to 14, when the staple cartridge assembly 40 is in the initial state of first firing, the firing block 49 and the cutter 45 are both located at the proximal end of the staple cartridge assembly 40; the firing block 49 does not contact the cutter 45; and the elastic piece 50 is located in the first notch 472 and is kept at the initial state.

Referring to FIGS. 15 to 19, when the staple cartridge assembly 40 enters a closing process, the cutting push rod 47 drives the cutter 45 to move toward the distal end of the staple cartridge assembly 40; the resisting end 501 of the elastic piece 50 resists against the boss 471 of the cutting push rod 47; and the elastic piece 50 acts on the distal end of the cutting push rod 47 to shift toward the staple cartridge channel 43 side, so that the protrusion 453 on the cutter 45 enters the groove 432, and the staple cartridge assembly 40 enters the secure state. At this time, the distal end of the second resisting portion 454 of the cutter 45 starts to contact the guiding portion 4911 of the first resisting portion 491 of the firing block 49, and the elastic piece 50 remains at the initial state.

Referring to FIGS. 20 to 24, when the staple cartridge assembly 40 continues to close, the cutting push rod 47 continues to drive the cutter 45 to move toward the distal end of the staple cartridge assembly 40; the firing block 49 remains stationary; and the second resisting portion 454 climbs up to a position above the first resisting portion 491 through the guiding portion 4911. At this time, the cutter 45 moves up to allow the protrusion 453 to be separated from the groove 432; and the staple cartridge assembly 40 is released from the secure state. Meanwhile, the boss 471 passes over the elastic piece 50 to reset the cutting push rod 47 connected to the cutter 45; and the boss 471 of the cutting push rod 47 extrudes the elastic piece 50 to cause the elastic piece 50 to deform toward a side away from the boss 471.

Referring to FIGS. 25 to 29, when the staple cartridge assembly 40 enters a fully closing process, the cutting push rod 47 drives the cutter 45 and the firing block 49 to move toward the distal end of the staple cartridge assembly 40 together until the staple cartridge assembly 40 is completely closed; the elastic piece 50 is separated from the boss 471 and then enters the second notch 473 to return to the initial state; and then the cutting push rod 47 drives the cutter 45 and the firing block 49 to perform the cutting and suturing operation.

Referring to FIGS. 30 to 34, when the staple cartridge assembly 40 enters the closing process for the second time, the cutting push rod 47 drives the cutter 45 to move toward the distal end of the staple cartridge assembly 40; the resisting end 501 of the elastic piece 50 resists against the boss 471 of the cutting push rod 47; and the elastic piece 50 acts on the distal end of the cutting push rod 47 to shift toward the staple cartridge channel 43 side, so that the protrusion 453 on the cutter 45 enters the groove 432. At this time, the firing block 49 is located at the distal end of the staple cartridge assembly 40; the cutter 45 is incapable of moving up; the protrusion 453 may not be separated from the groove 432; and the staple cartridge assembly 40 remains at the secure state, thereby preventing secondary firing.

Referring to FIG. 35 to FIG. 65 which show the schematic diagrams of the staple cartridge assembly 40a according to a second embodiment of the present invention.

For convenience of explanation, similar components in the second embodiment are designated with the same names as those in the first embodiment, and are distinguished by different numbers.

Figure 35:
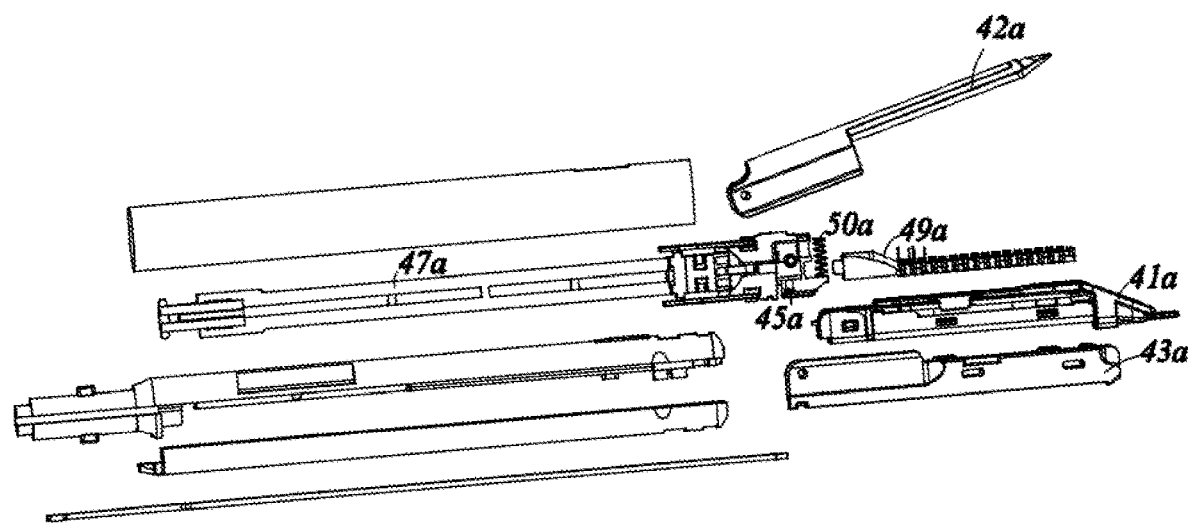
FIG. 35 is a schematically exploded diagram of a staple cartridge assembly according to a second embodiment of the present invention.
Figure 36:
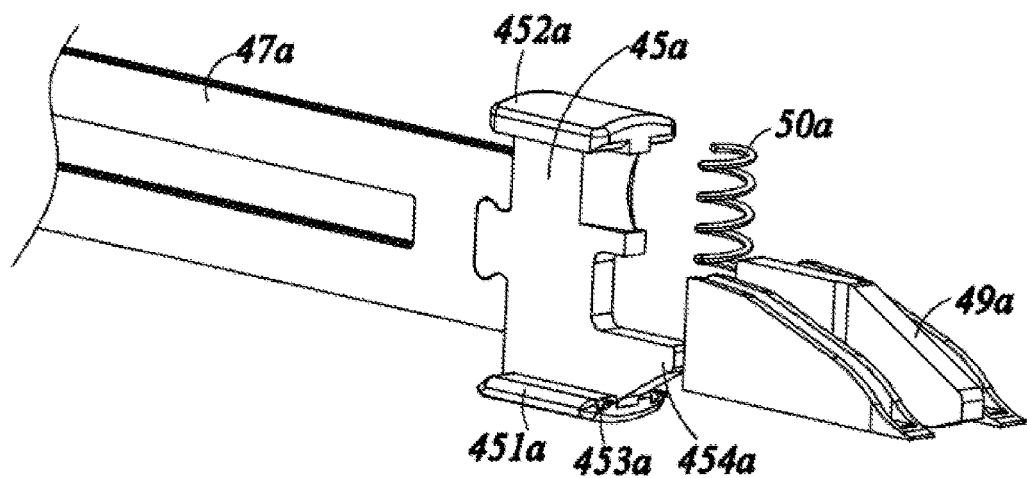
FIG. 36 is a schematic diagram of a combination of a cutting push rod, a cutter and a firing block according to the second embodiment of the present invention.
Figure 37:
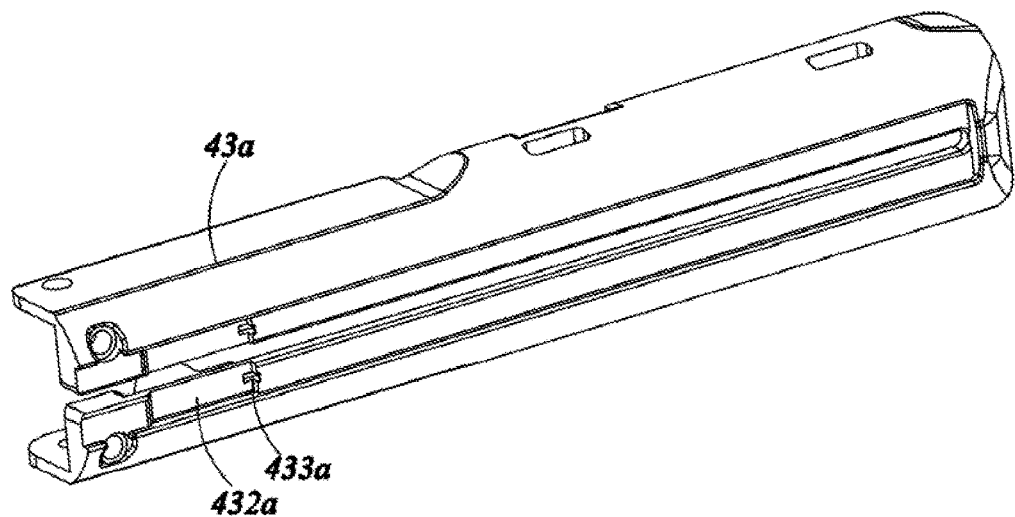
FIG. 37 is a schematic diagram of a staple cartridge channel according to the second embodiment of the present invention.
Figure 38:
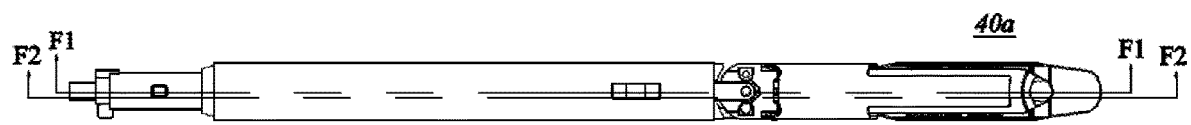
FIG. 38 is a schematic diagram of the staple cartridge assembly according to the second embodiment of the present invention, which is in an initial state.
Figure 39:
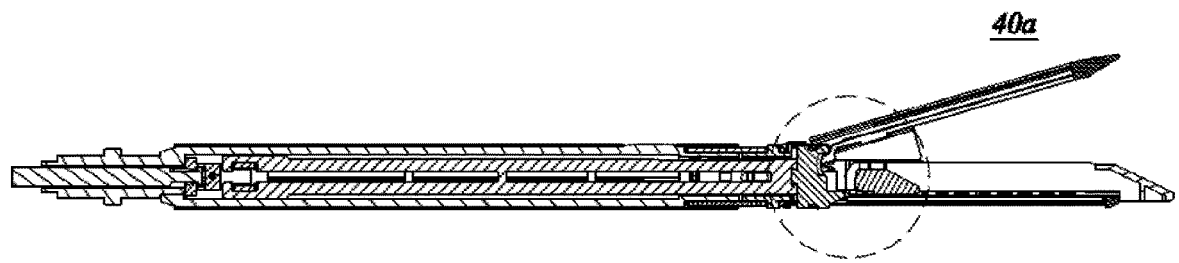
FIG. 39 is a sectional view along F1-F1 in FIG. 38.
Figure 40:
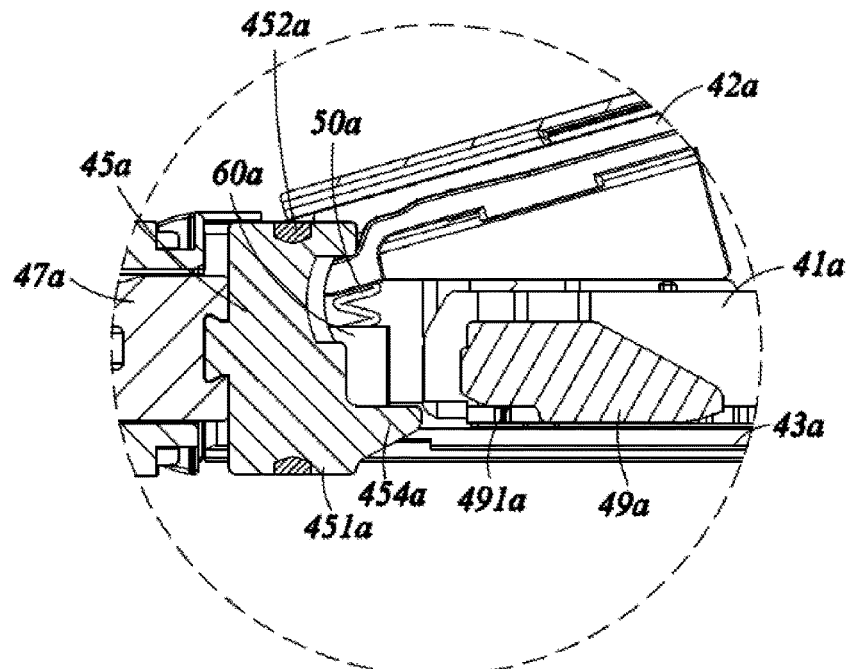
FIG. 40 is an enlarged view of a partial area in FIG. 39.
Figure 41:
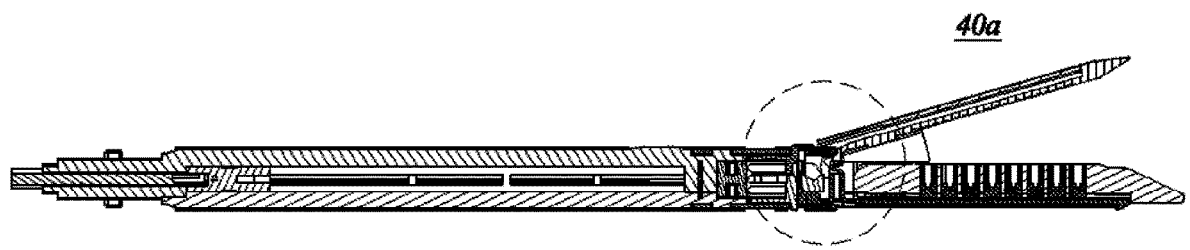
FIG. 41 is a sectional view along F2-F2 in FIG. 38.
Figure 42:
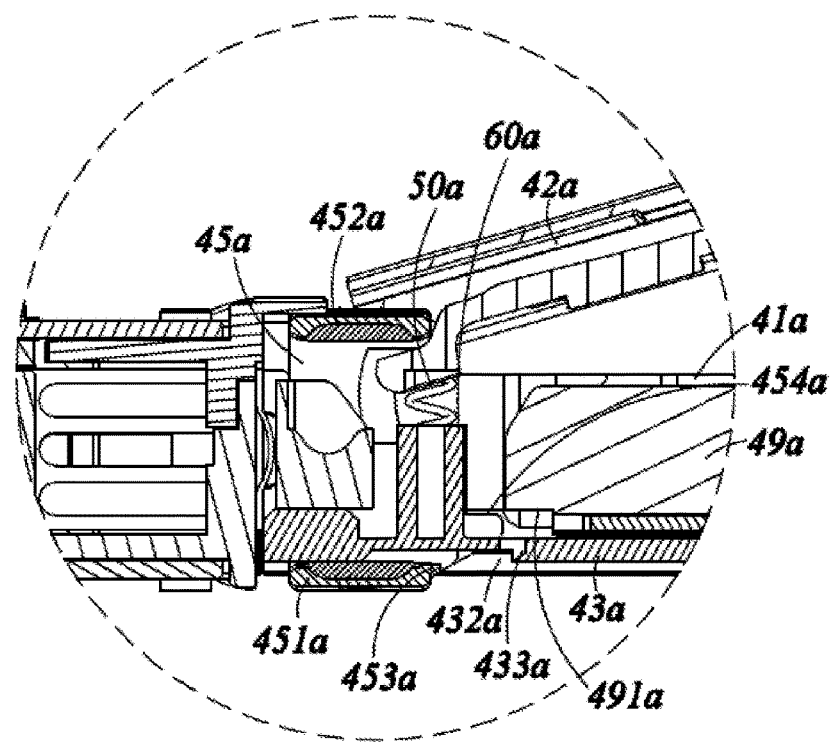
FIG. 42 is an enlarged view of a partial area in FIG. 41.
Figure 43:
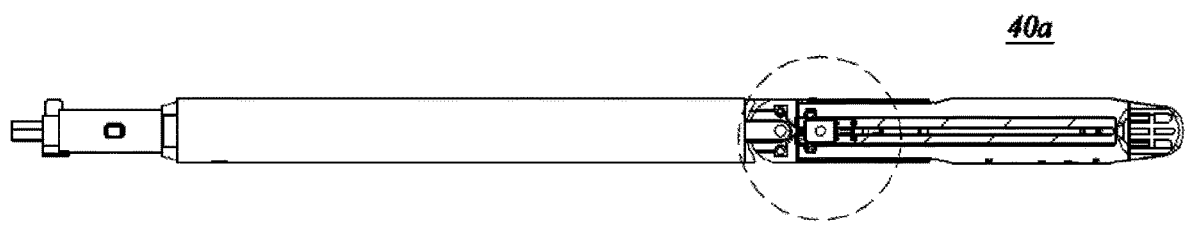
FIG. 43 is a bottom view of the staple cartridge assembly according to the second embodiment of the present invention, which is in the initial state.
Figure 44:
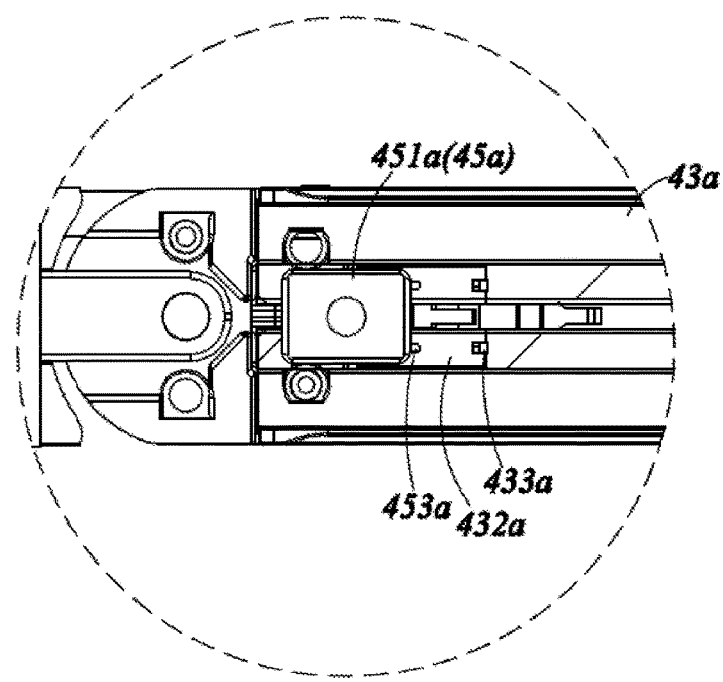
FIG. 44 is an enlarged view of a partial area in FIG. 43.
Figure 45:
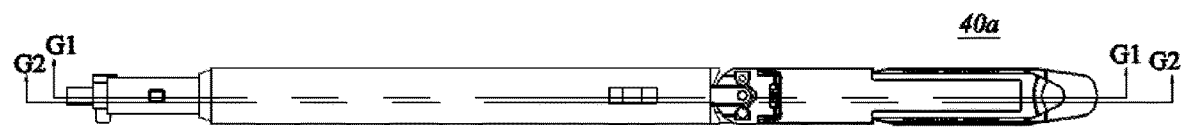
FIG. 45 is a schematic diagram of the staple cartridge assembly according to the second embodiment of the present invention, which enters a closing process.
Figure 46:
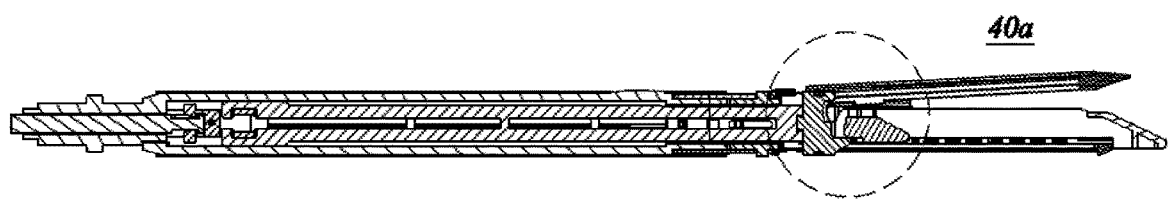
FIG. 46 is a sectional view along G1-G1 in FIG. 45.
Figure 47:
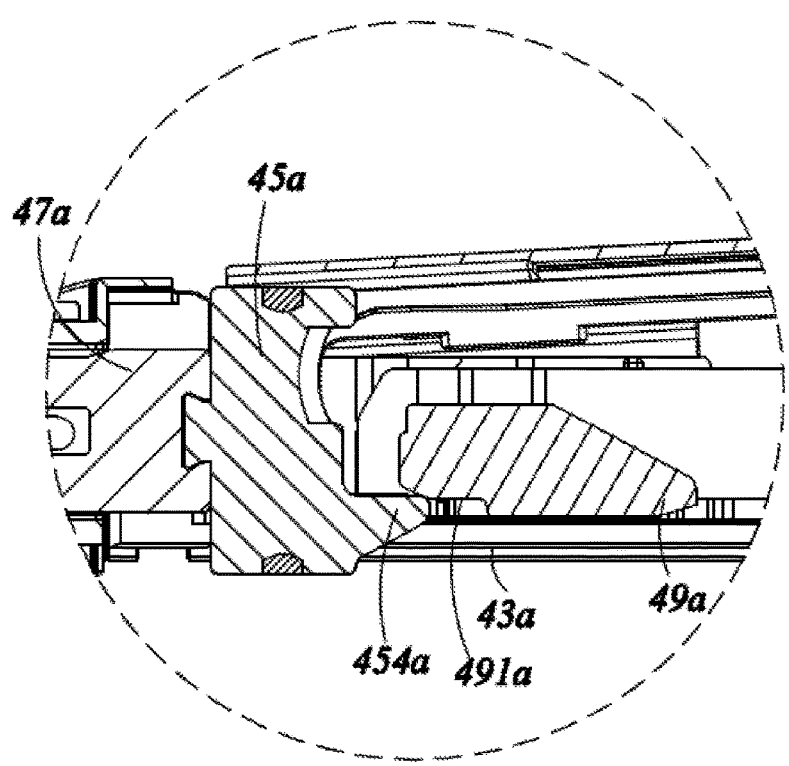
FIG. 47 is an enlarged view of a partial area in FIG. 46.
Figure 48:
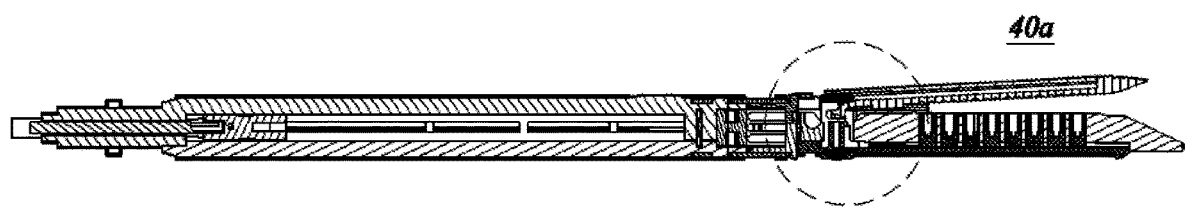
FIG. 48 is a sectional view along G2-G2 in FIG. 45.
Figure 49:
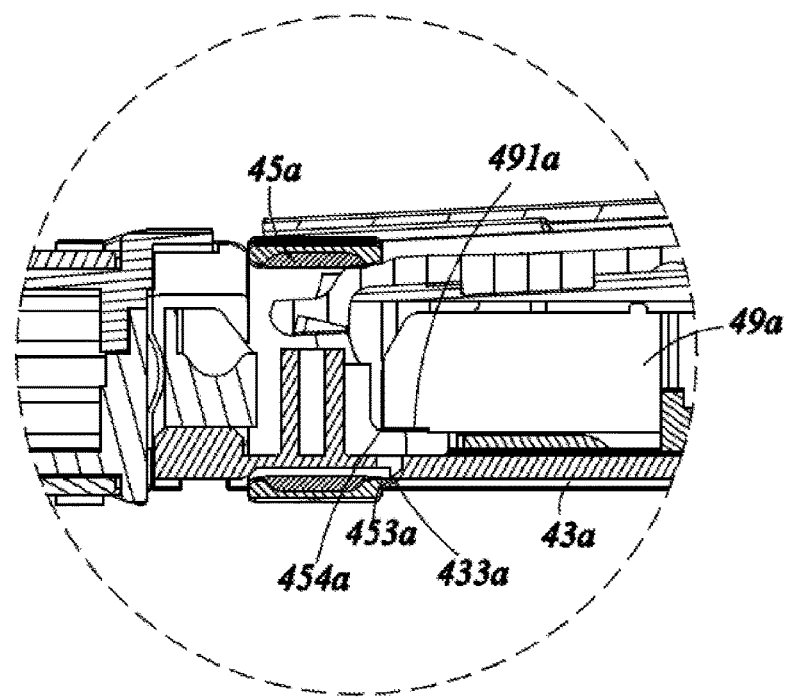
FIG. 49 is an enlarged view of a partial area in FIG. 48.
Figure 50:
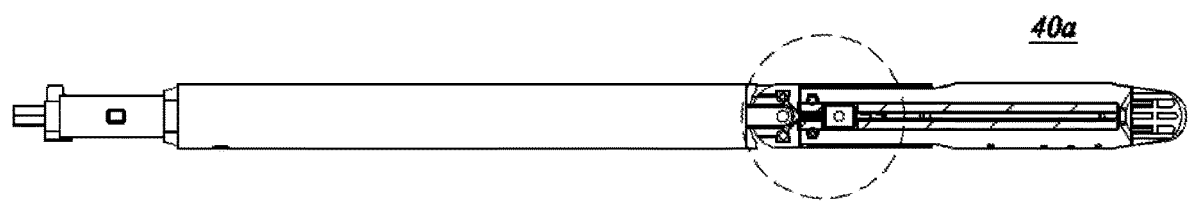
FIG. 50 is a bottom view of the staple cartridge assembly according to the second embodiment of the present invention, which enters the closing process.
Figure 51:
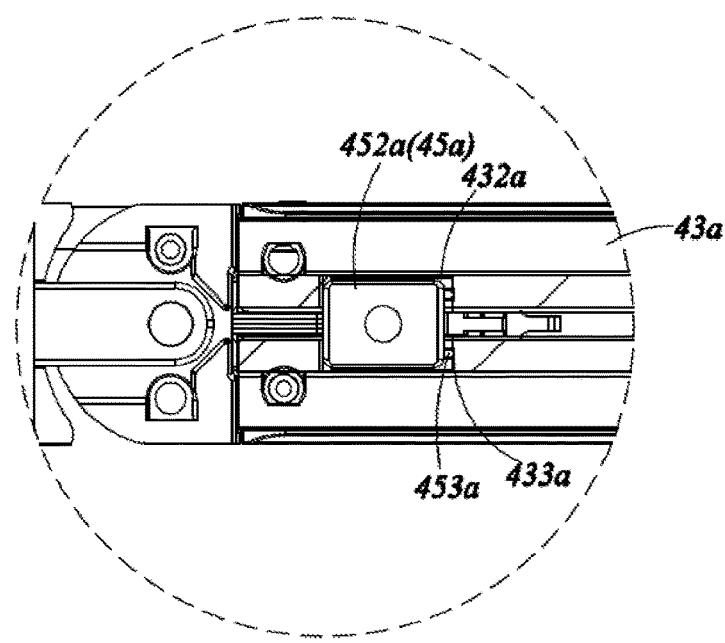
FIG. 51 is an enlarged view of a partial area in FIG. 50.
Figure 52:
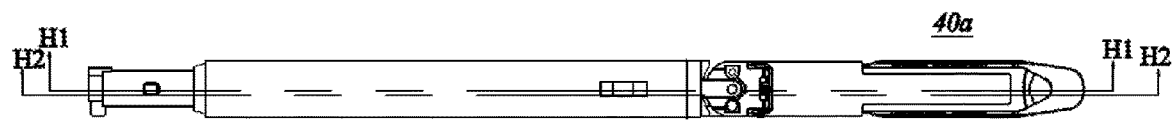
FIG. 52 is a schematic diagram of the staple cartridge assembly according to the second embodiment of the present invention, which is fully closed.
Figure 53:
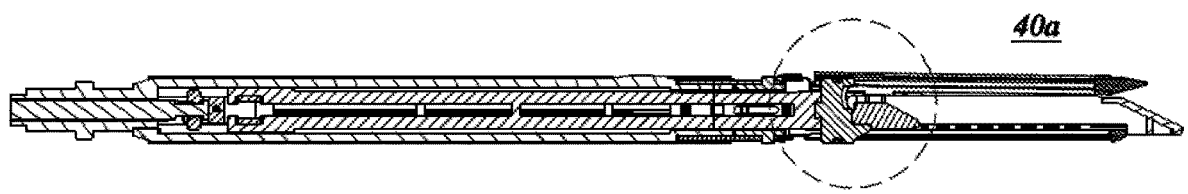
FIG. 53 is a sectional view along H1-H1 in FIG. 52.
Figure 54:
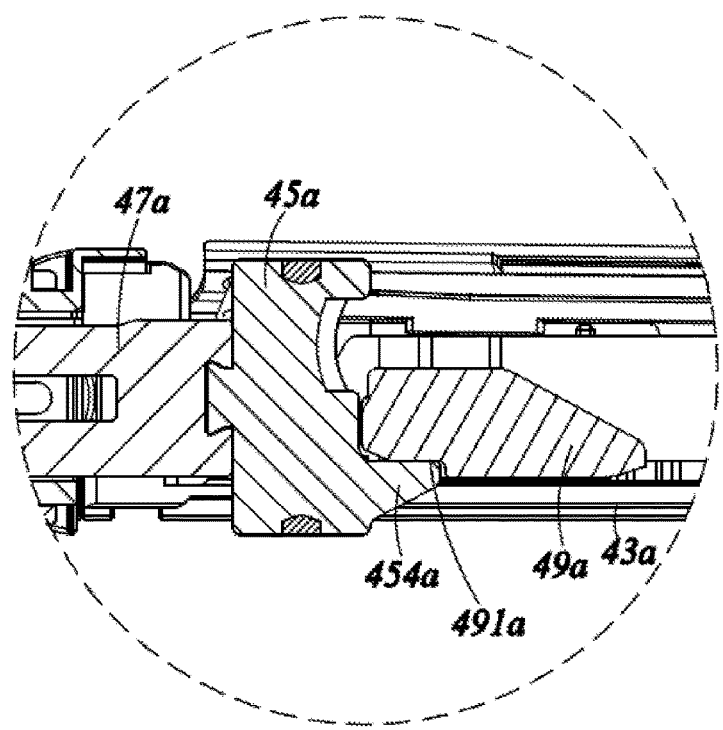
FIG. 54 is an enlarged view of a partial area in FIG. 53.
Figure 55:
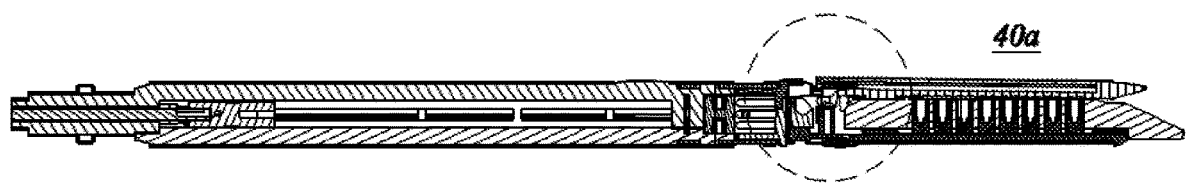
FIG. 55 is a sectional view along H2-H2 in FIG. 52.
Figure 56:
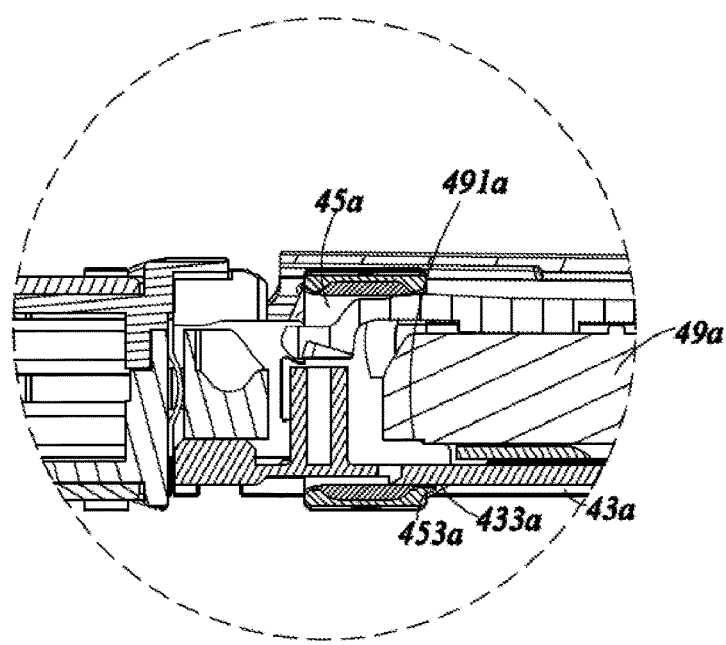
FIG. 56 is an enlarged view of a partial area in FIG. 55.
Figure 57:
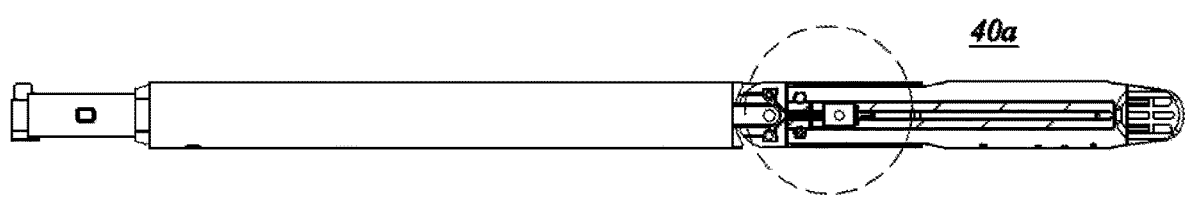
FIG. 57 is a bottom view of the staple cartridge assembly according to the second embodiment of the present invention, which is fully closed.
Figure 58:
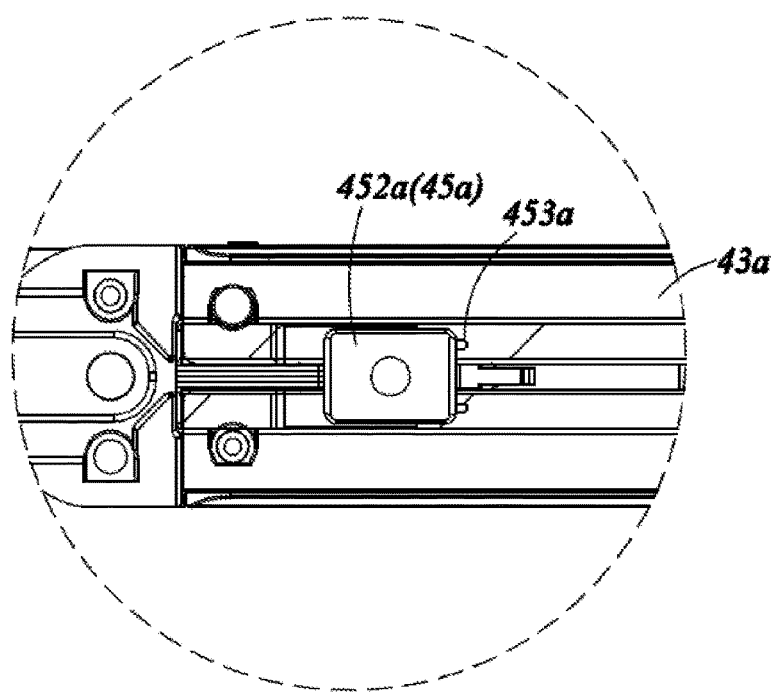
FIG. 58 is an enlarged view of a partial area in FIG. 57.
Figure 59:
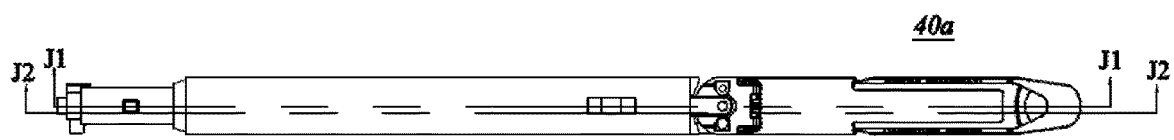
FIG. 59 is a schematic diagram of the staple cartridge assembly according to the second embodiment of the present invention, which enters the secondary closing process.
Figure 60:
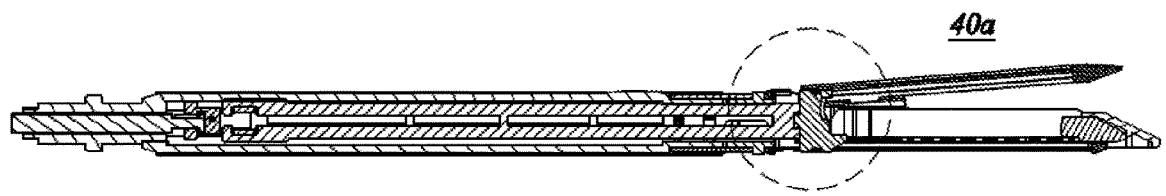
FIG. 60 is a sectional view along J1-J1 in FIG. 59.
Figure 61:
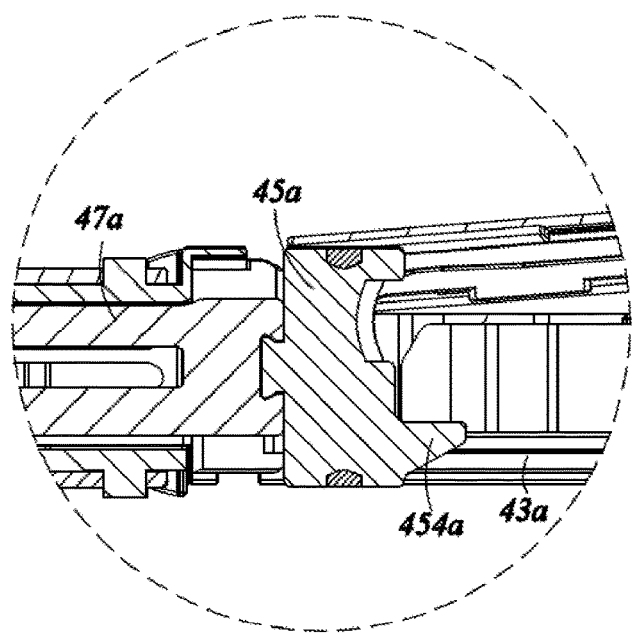
FIG. 61 is an enlarged view of a partial area in FIG. 60.
Figure 62:
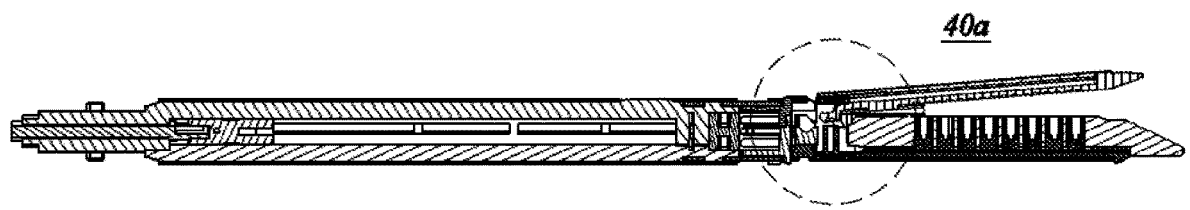
FIG. 62 is a sectional view along J2-J2 in FIG. 59.
Figure 63:
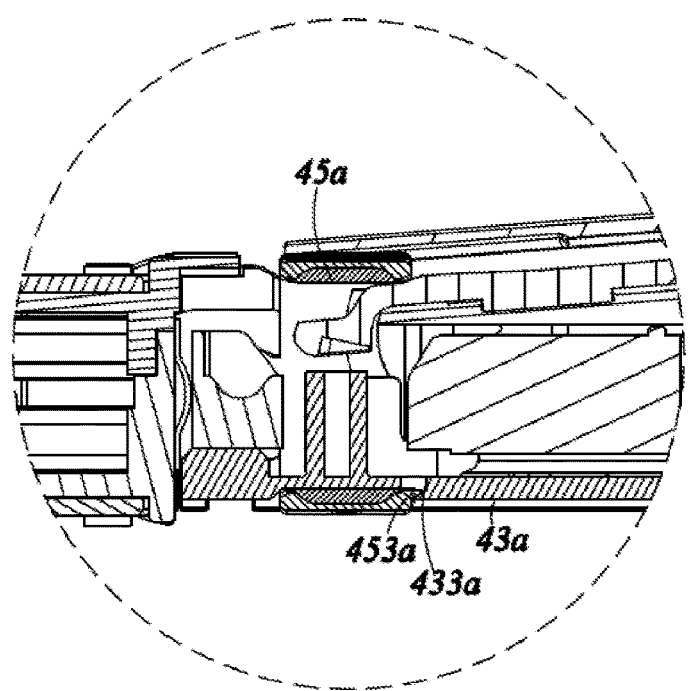
FIG. 63 is an enlarged view of a partial area in FIG. 62.
Figure 64:
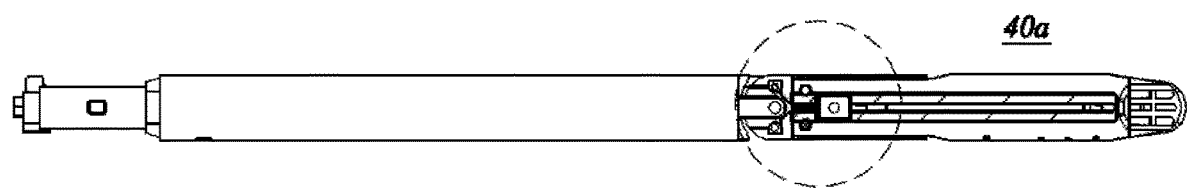
FIG. 64 is a bottom view of the staple cartridge assembly according to the second embodiment of the present invention, which enters the secondary closing process.
Figure 65:
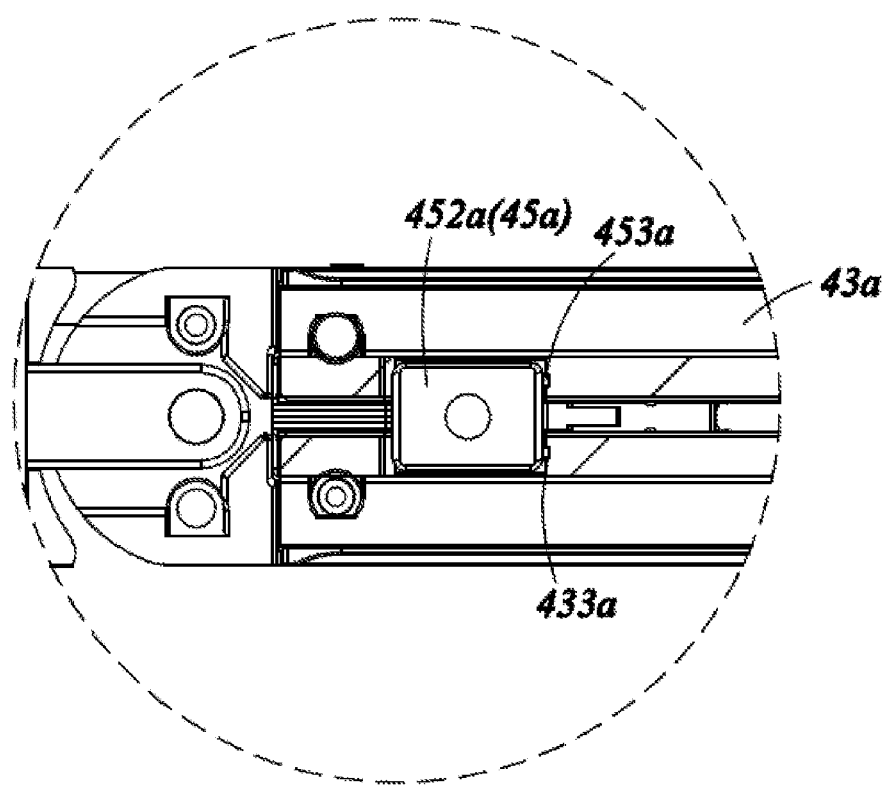
FIG. 65 is an enlarged view of a partial area in FIG. 64.

In this embodiment, referring to FIGS. 35 to 37, the driving mechanism 50 is a compression spring 50a that is located at the proximal end of the staple cartridge assembly 40a and connects the staple cartridge channel 43a and the anvil 42a. The compression spring 50a acts on the distal ends of the staple cartridge 41 and the anvil 42, so that the first jaw and the second jaw are open in the initial state. When the cutting push rod 47a drives the cutter 45a to move toward the distal end of the staple cartridge assembly 40a and to the limiting portion (including a receiving groove 432a in the outer surface of the staple cartridge channel 43a and a recessed portion 433a at the distal end of the receiving groove 432a, see the detailed description below), the compression spring 50a drives the staple cartridge channel 43a to shift toward a side close to the securing portion (including a first end 451a of the cutter 45a and a bulging portion 453a located at the distal end of the first end 451a, see the detailed description below), causing the securing portion to enter the limiting portion.

A first contact portion 491a is disposed at the proximal end of the firing block 49a, and a second contact portion 454a is disposed at the distal end of the cutter 45a. When the first contact portion 491a and the second contact portion 454a resist against each other, the firing block 49a drives the cutter 45a to shift toward a side away from the staple cartridge channel 43a to allow the securing portion 453a to be separated from the limiting portion 432a.

At least one of the first contact portion 491a and the second contact portion 454a is provided with a guiding portion. Here, an arcuate face 4911a at the proximal end of the first contact portion 491a is taken as the guiding portion 4911a. When the cutter 45a moves toward the distal end of the staple cartridge assembly 40a with respect to the firing block 49a, the firing block 49a smoothly presses the cutter 45a down through the guiding portion 4911a, so that the securing portion moves down to be separated from the limiting portion.

In this embodiment, the limiting portion includes the receiving groove 432a in the outer surface of the staple cartridge channel 43a. The securing portion includes the first end 451a of the cutter 45a. The first end 451a is located at the outer surface of the staple cartridge channel 43a. When the cutter 45a moves to the receiving groove 432a, the compression spring 50a acts on the staple cartridge channel 43a to allow the first end 451a to enter the receiving groove 432a. When the firing block 49a abuts against the cutter 45a, the firing block 49a drives the first end 451a to shift toward a side away from the staple cartridge channel 43a, thereby allowing the first end 451a to be separated from the receiving groove 432a.

The limiting portion further includes the recessed portion 433a located at the distal end of the receiving groove 432a. The securing portion further includes a bulging portion 453a located at the distal end of the first end 451a. When the first end 451a is located in the receiving groove 432a and the cutter 45a continues moving toward the distal end of the staple cartridge assembly 40a, the bulging portion 453a and the recessed portion 433a are engaged with each other to ensure the secure effect.

Here, the limiting portion includes two recessed portions 433a that are symmetrically distributed at the distal end of the receiving groove 432a, and the securing portion includes two bulging portions 453a that are symmetrically distributed at the distal end of the first end 451a.

In this embodiment, the driving mechanism 50 includes a compression spring 50a located on one side of the cutter 45a. The staple cartridge channel 43a is provided with a receiving chamber 60a for receiving the compression spring 50a. Of course, the driving mechanism 50 may include two compression springs 50a that are symmetrically distributed on two sides of the cutter 45a.

Next, the working principle of the staple cartridge assembly 40a of this embodiment will be described in detail below.

Referring to FIGS. 38 to 44, when the staple cartridge assembly 40a is in the initial state of the first firing, the firing block 49a and the cutter 45a are both located at the proximal end of the staple cartridge assembly 40a; the firing block 49a does not contact the cutter 45a; and the first end 451a of the cutter 45a is located at the outer surface of the staple cartridge channel 43a and at the proximal end of the receiving groove 432a.

Referring to FIGS. 45 to 51, when the staple cartridge assembly 40a enters the closing process, the cutting push rod 47a drives the cutter 45a to move toward the distal end of the staple cartridge assembly 40a. When the first end 451a of the cutter 45a moves to the receiving groove 432a, since the compression spring 50a always drives the staple cartridge assembly 40a to open at the maximal opening angle at the distal end, the compression spring 50a at this time drives the staple cartridge channel 43a to move away from the anvil 42a; the first end 451a just falls into the receiving groove 432a; the staple cartridge assembly 40a enters the secure state; and the distal end of the second contact portion 454a of the cutter 45a starts to contact the guiding portion 4911a of the first contact portion 491a of the firing block 49a. When the cutter 45a continues moving toward the distal end of the staple cartridge assembly 40a, the firing block 49a remains stationary; and the firing block 49a extrudes the cutter 45a through the interaction between the first contact portion 491a and the second contact portion 454a, to move the first end 451a downward. As a result, the first end 451a is separated from the receiving groove 432a, and the staple cartridge assembly 40a is released from the secure state.

Referring to FIGS. 52 to 58, when the staple cartridge assembly 40a enters a fully closing process, the cutting push rod 47a drives the cutter 45a and the firing block 49a to move toward the distal end of the staple cartridge assembly 40a together until the staple cartridge assembly 40a is completely closed; and then the cutting push rod 47a drives the cutter 45a and the firing block 49a to perform the cutting and suturing operation.

Similarly, when "the distance between the firing block 49 and the cutter 45 is relatively smaller", that is, during the first closing, the firing block 49 acts on the cutter 45 to prevent the securing portion 453 from entering the limiting portion 432, and the staple cartridge assembly 40 enters the secure state, so that the stapler can be fired. When the firing is completed, the firing block 49 remains at the distal end of the staple cartridge 41 and there is no resistance against the cutter 45 from the firing block 49, so that the securing portion 453 cannot be separated from the limiting portion 432 to reach the secure state.

Referring to FIGS. 59 to 65, when the staple cartridge assembly 40a enters the closing process for the second time, the cutting push rod 47a drives the cutter 45a to move toward the distal end of the staple cartridge assembly 40a. When the first end 451a of the cutter 45a moves to the receiving groove 432a, since the compression spring 50a always drives the staple cartridge assembly 40a to open at the maximal opening angle at the distal end, the compression spring 50a at this time drives the staple cartridge channel 43a to move away from the anvil 42a; and the first end 451a just falls into the receiving groove 432a. At this time, the firing block 49a is located at the distal end of the staple cartridge assembly 40a; the cutter 45a cannot move down; the first end 451a cannot be separated from the receiving groove 432a; and the staple cartridge assembly 40 remains at the secure state, thereby preventing the secondary firing. Here, when the cutter 45a continues moving toward the distal end of the staple cartridge assembly 40a, the bulging portion 453a and the recessed portion 433a are engaged with each other, so that the cutter 45a and the staple cartridge channel 43a cooperate more firmly and the higher security is achieved. It should be noted that the two embodiments above are merely for illustrating the staple cartridge assembly 40 of the present invention by way of example, and the two embodiments can also be combined, replaced, or otherwise operated to form a new embodiment. For example, the first embodiment can also include a compression spring for controlling the opening angle at the distal end of the staple cartridge assembly 40.

It should be understood that although the present invention is described in terms of embodiments in this description, not every embodiment includes only one independent technical solution. The statement mode of the description is merely for clarity, and those skilled in the art should regard the description as a whole, where the technical solutions in various embodiments may also be combined properly to develop other embodiments that can be understood by those skilled in the art.

The series of detailed illustration listed above are merely for specifically illustrating the feasible embodiments of the present invention, but not intended to limit the protection scope of the present invention. Any equivalent embodiments or variations made without departing from the technical spirit of the present invention shall fall within the protection scope of the present invention.

What is claimed is:

1. A staple cartridge assembly, comprising:
    a staple cartridge connector, which comprises a housing and a cutting push rod located in the housing;
    a first jaw and a second jaw, both of which are located at a distal end of the staple cartridge connector and are capable of being opened/closed;
    a firing block, which is movably disposed in the first jaw or the second jaw;
    a cutter, which is located at a distal end of the cutting push rod, and can push the firing block to move when the cutting push rod pushes the cutter to move; and
    a driving mechanism;
    wherein the first jaw is provided with a limiting portion at a proximal end; the cutter is provided with a securing portion; when the firing block is located at a proximal end of the staple cartridge assembly, the cutting push rod pushes the cutter and the firing block to move together toward a distal end of the staple cartridge assembly; when the firing block is located at the distal end of the staple cartridge assembly, the driving mechanism pushes the cutter to move relative to the first jaw via the cutting push rod; and the limiting portion and the securing portion resist against each other to restrict the cutter from continuing moving toward the distal end of the staple cartridge assembly; and
    when the firing block is located at the proximal end of the staple cartridge assembly and the cutter does not contact the firing block, the driving mechanism pushes the cutter to move relative to the first jaw via the cutting push rod, and the securing portion enters and stays in the limiting portion before any contact between the cutter and the firing block; and then when the cutting push rod continues pushing the cutter to move toward the distal end of the staple cartridge assembly, the firing block abuts against the cutter and moves the cutter to shift away from the first jaw, and the securing portion leaves the limiting portion and is separated from the limiting portion.

2. The staple cartridge assembly according to claim 1, wherein the first jaw comprises a staple cartridge channel and a staple cartridge, which are connected; the second jaw is an anvil; and the limiting portion is located at the staple cartridge channel.

3. The staple cartridge assembly according to claim 2, wherein the driving mechanism is a driving member connected to the housing; the cutting push rod is provided with a boss at a side close to the driving member; and when the boss moves toward the distal end of the staple cartridge assembly and to the driving member, the driving member pushes the cutting push rod to shift away from the driving member, so that the cutter shifts close to the staple cartridge channel to allow the securing portion to enter the limiting portion.

4. The staple cartridge assembly according to claim 3, wherein the firing block is provided with a first resisting portion at a proximal end; the cutter is provided with a second resisting portion at a distal end; and when the first resisting portion and the second resisting portion resist against each other, the firing block pushes the cutter to shift away from the staple cartridge channel to allow the securing portion to be separated from the limiting portion.

5. The staple cartridge assembly according to claim 4, wherein at least one of the first resisting portion and the second resisting portion is provided with a guiding portion.

6. The staple cartridge assembly according to claim 3, wherein one of the securing portion and the limiting portion is a protrusion, and the other is a groove.

7. The staple cartridge assembly according to claim 3, wherein the securing portion is a protrusion, which comprises a first slope at a proximal end; the limiting portion is a groove, which comprises a second slope at a proximal end; and the first slope and the second slope are the same in gradient.

8. The staple cartridge assembly according to claim 7, wherein the protrusion comprises a first plane at a distal end; the groove comprises a second plane at a distal end; and when the protrusion is located at the most distal end of the groove, the first plane and the second plane interfere with each other to restrict the protrusion from being separated from the groove.

9. The staple cartridge assembly according to claim 3, wherein the driving member is an elastic piece; when the boss moves toward the distal end of the staple cartridge assembly and to the elastic piece, the elastic piece pushes the cutting push rod to shift away from the elastic piece; and when the firing block abuts against the cutter, the firing block pushes the cutter to shift away from the staple cartridge channel to allow the cutting push rod to reset, and the boss drives the elastic piece to deform away from the boss.

10. The staple cartridge assembly according to claim 9, wherein the cutting push rod is provided with notches on two sides of the boss; and when the elastic piece is separated from the boss, the elastic piece enters one of the notches and the elastic piece maintains an initial state.

11. The staple cartridge assembly according to claim 9, wherein the elastic piece is a U-shaped elastic piece.

12. The staple cartridge assembly according to claim 2, wherein the driving mechanism is a compression spring that is located at the proximal end of the staple cartridge assembly and connected to the staple cartridge channel and the anvil; when the cutting push rod pushes the cutter to move toward the distal end of the staple cartridge assembly and to the limiting portion, the compression spring pushes the staple cartridge channel to shift close to the securing portion to allow the securing portion to enter the limiting portion.

13. The staple cartridge assembly according to claim 12, wherein the firing block is provided with a first contact portion at its proximal end; the cutter is provided with a second contact portion at its distal end; and when the first contact portion and the second contact portion resist against each other, the firing block pushes the cutter to shift away from the staple cartridge channel to allow the securing portion to be separated from the limiting portion.

14. The staple cartridge assembly according to claim 13, wherein at least one of the first contact portion and the second contact portion is provided with a guiding portion.

15. The staple cartridge assembly according to claim 12, wherein the limiting portion comprises a receiving groove located in an outer surface of the staple cartridge channel; the securing portion comprises a first end of the cutter; the first end is located at the outer surface of the staple cartridge channel; when the cutter moves to the receiving groove, the compression spring acts on the staple cartridge channel to allow the first end to enter the receiving groove; and when the firing block abuts against the cutter, the firing block pushes the first end to shift away from the staple cartridge channel to allow the first end to be separated from the receiving groove.

16. The staple cartridge assembly according to claim 15, wherein the limiting portion further comprises a recessed portion located at a distal end of the receiving groove; the securing portion further comprises a bulging portion located at a distal end of the first end; and when the first end is located in the receiving groove and the cutter continues to move toward the distal end of the staple cartridge assembly, the bulging portion and the recessed portion are engaged with each other.

17. The staple cartridge assembly according to claim 16, wherein the limiting portion comprises two recessed portions that are symmetrically distributed at the distal end of the receiving groove; and the securing portion comprises two bulging portions that are symmetrically distributed at the distal end of the first end.

18. The staple cartridge assembly according to claim 12, wherein the driving mechanism comprises two compression springs that are symmetrically distributed on two sides of the cutter.

19. A medical stapler, comprising a staple cartridge assembly according to claim 1.

* * * * *